(12) United States Patent
Lee et al.

(10) Patent No.: US 11,065,356 B2
(45) Date of Patent: *Jul. 20, 2021

(54) MAGNETIC SEPARATION USING NANOPARTICLES

(71) Applicants: Children's Medical Center Corporation, Boston, MA (US); Massachusetts Institute of Technology, Cambridge, MA (US)

(72) Inventors: Jung-Jae Lee, Chestnut Hill, MA (US); Kyung Jae Jeong, Chestnut Hill, MA (US); Daniel S. Kohane, Newton, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,151

(22) Filed: Jul. 15, 2019

(65) Prior Publication Data

US 2019/0336635 A1    Nov. 7, 2019

Related U.S. Application Data

(63) Continuation of application No. 14/167,773, filed on Jan. 29, 2014, now Pat. No. 10,350,320.
(Continued)

(51) Int. Cl.
*A61L 9/00* (2006.01)
*A61L 2/00* (2006.01)

(52) U.S. Cl.
CPC .. *A61L 9/00* (2013.01); *A61L 2/00* (2013.01)

(58) Field of Classification Search
None
See application file for complete search history.

(56) References Cited

U.S. PATENT DOCUMENTS

| 5,185,313 A | 2/1993 | Porath |
| 8,304,230 B2 | 11/2012 | Toner et al. |

(Continued)

FOREIGN PATENT DOCUMENTS

WO    2010/151085    12/2010

OTHER PUBLICATIONS

Bromberg et al., "Binding of Functionalized Paramagnetic Nanoparticles to Bacterial Lipopolysacchardies and DNA," Langmuir, 2010, 26(11):8829-8835.
(Continued)

*Primary Examiner* — Matthew D Krcha
(74) *Attorney, Agent, or Firm* — Fish & Richardson P.C.

(57) ABSTRACT

Nanoparticles as described herein are configured to bind to bacterial contaminants, such as Gram positive bacteria, Gram negative bacteria, and endotoxins. The nanoparticles include a core comprising a magnetic material; and a plurality of ligands attached to the core. The ligands include, for example, bis(dipicolylamine) ("DPA") coordinated with a metal ion, e.g., $Zn^{2+}$ or $Cu^{2+}$, to form, e.g., bis-Zn-DPA or bis-Cu-DPA, which can bind to the bacterial contaminants. The nanoparticles can be included in compositions for use in methods and systems to separate bacterial contaminants from liquids, such as liquids, such as blood, e.g., whole or diluted blood, buffer solutions, albumin solutions, beverages for human and/or animal consumption, e.g., drinking water, liquid medications for humans and/or animals, or other liquids.

14 Claims, 20 Drawing Sheets

Related U.S. Application Data

(60) Provisional application No. 61/758,046, filed on Jan. 29, 2013.

(56) References Cited

U.S. PATENT DOCUMENTS

| | | | |
|---|---|---|---|
| 2007/0134648 A1* | 6/2007 | Soskic | C07K 1/22 435/4 |
| 2009/0220932 A1* | 9/2009 | Ingber | G01N 15/1484 435/2 |
| 2009/0233373 A1 | 9/2009 | Hamachi et al. | |
| 2010/0047895 A1 | 2/2010 | Schutz et al. | |
| 2011/0262989 A1 | 10/2011 | Clarizia et al. | |
| 2012/0018382 A1* | 1/2012 | Stein | B03C 1/00 210/663 |

OTHER PUBLICATIONS

Burry, "Antibodies," Immunocytochemistry, 2010, pp. 7-16 (Abstract).
Chapman, "PEGylated antibodies and antibody fragments for improved therapy: a review," Adv. Drug Deliver. Rev., 2002, 54(4):531-545.
Choi et al., "Synthesis, properties, and X-ray structure of [Cu(dpa)Cl2] (dpa=di-(2-picolyl)amine)," Journal of Chemical Crystallography, 33(12):947-950 (2003).
El-Boubbou et al., "Magnetic Glyco-nanoparticles: A Unique Tool for Rapid Pathogen Detection, Decontamination, and Strain Differentiation," J. Am. Chem. Soc., 2007, 129(44):13392-13393.
Helton and Yager, "Interfacial instabilities affect microfluidic extraction of small molecules from non-Newtonian fluids," Lab Chip, 2007, 7(11):1581-1588.
Hou et al., "A microfluidics approach towards high-throughput pathogen removal from blood using margination," J. Biomicrofluidics, 2012, 6(2):24115-2411513.
International Search Report and Written Opinion issued in PCT/US2014/013633 dated May 9, 2014.
Jia et al., "Catalytic behaviors of enzymes attached to nanoparticles: the effect of particle mobility," Biotech. Bioeng., 2003, 84(4):406-414.
Kohane, "Microparticles and nanoparticles for drug delivery," Biotech. Bioeng., 2007, 96(2):203-209.
Lakshmi et al., "Fluorophore-linked zinc(II)dipicolylamine coordination complexes as sensors for phosphatidylserine-containing membranes," Tetrahedron, 2004, 60(49):11307-11315.
Leevy et al., "Noninvasive Optical Imaging of *Staphylococcus aureus* Bacterial Infection in Living Mice Using a Bis-Dipicolylamine-Zinc(II) Affinity Group Conjugated to a Near-Infrared Fluorophore," Bioconjugate Chem., 2008, 19(3):686-692.
Leevy et al., "Optical Imaging of Bacterial Infection in Living Mice Using a Fluorescent Near-Infrared Molecular Probe," J. Am. Chem. Soc. 2006, 128(51):16476-16477.
Leevy et al., "Selective recognition of bacterial membranes by zinc(II)-coordination complexes," Chem. Comm. 2006, (15):1595-1597.
Lenshof and Laurell, "Continuous separation of cells and particles in microfluidic systems," Chem. Soc. Rev., 2010, 39(3):1203-1217.
Mach and Di Carlo, "Continuous scalable blood filtration device using inertial microfluidics," Biotech. Bioeng., 2010, 107(2):302-311.
Ngo et al., "Anion recognition and sensing with Zn(II)-dipicolylamine complexes," Chem. Soc. Rev., 2012, 41(14):4928-4965.
O'Neil and Smith, "Anion recognition using dimetallic coordination complexes," Coordin. Chem. Rev., 2006, 250(23-24):3068-3080.
Pamme, "Continuous flow separations in microfluidic devices," Lab Chip 2007, 7(12):1644-1659.
Qiu et al., "Immunomagnetic separation and rapid detection of bacteria using bioluminescence and microfluidics," Talanta 2009, 79(3):787-795 (Abstract ).
Shih et al., "On chip sorting of bacterial cells using sugar-encapsulated magnetic nanoparticles," J. Appl. Phys., 2008, 103:07A316.
Sia and Whitesides, "Microfluidic devices fabricated in Poly(dimethylsiloxane) for biological studies," Electrophoresis, 2003, 24(21):3563-3576.
Tajima et al., "Significance of Antibody Orientation Unraveled: Well-Oriented Antibodies Recorded High Binding Affinity," Anal. Chem., 2011, 83(6):1969-1976.
Thakur et al., "Targeting Apoptosis for Optical Imaging of Infection," Mol. Imaging. Biol., 2012, 14(2):163-171.
White et al., "Deep-red fluorescent imaging probe for bacteria," Bioorg. Med. Chem. Lett., 2012, 22(8):2833-2836.
Wu et al., "Soft inertial microfluidics for high throughput separation of bacteria from human blood cells," Lab Chip, 2009, 9(9):1193-1199.
Xia et al., "Combined microfluidic-micromagnetic separation of living cells in continuous flow," Biomed. Microdevices, 2006, 8(4):299-308.
Yung et al., "Micromagnetic-microfluidic blood cleansing device," Lab Chip, 2009, 9(9):1171-1177.
Zhang and Xu, "Maltifunctional Magnetic Nanoparticles as Bionanomaterials," Action Bioscience, Jul. 2011, 4 pages, http://www.actionbioscience.org/biotechnology/zhang_xu.html.

* cited by examiner

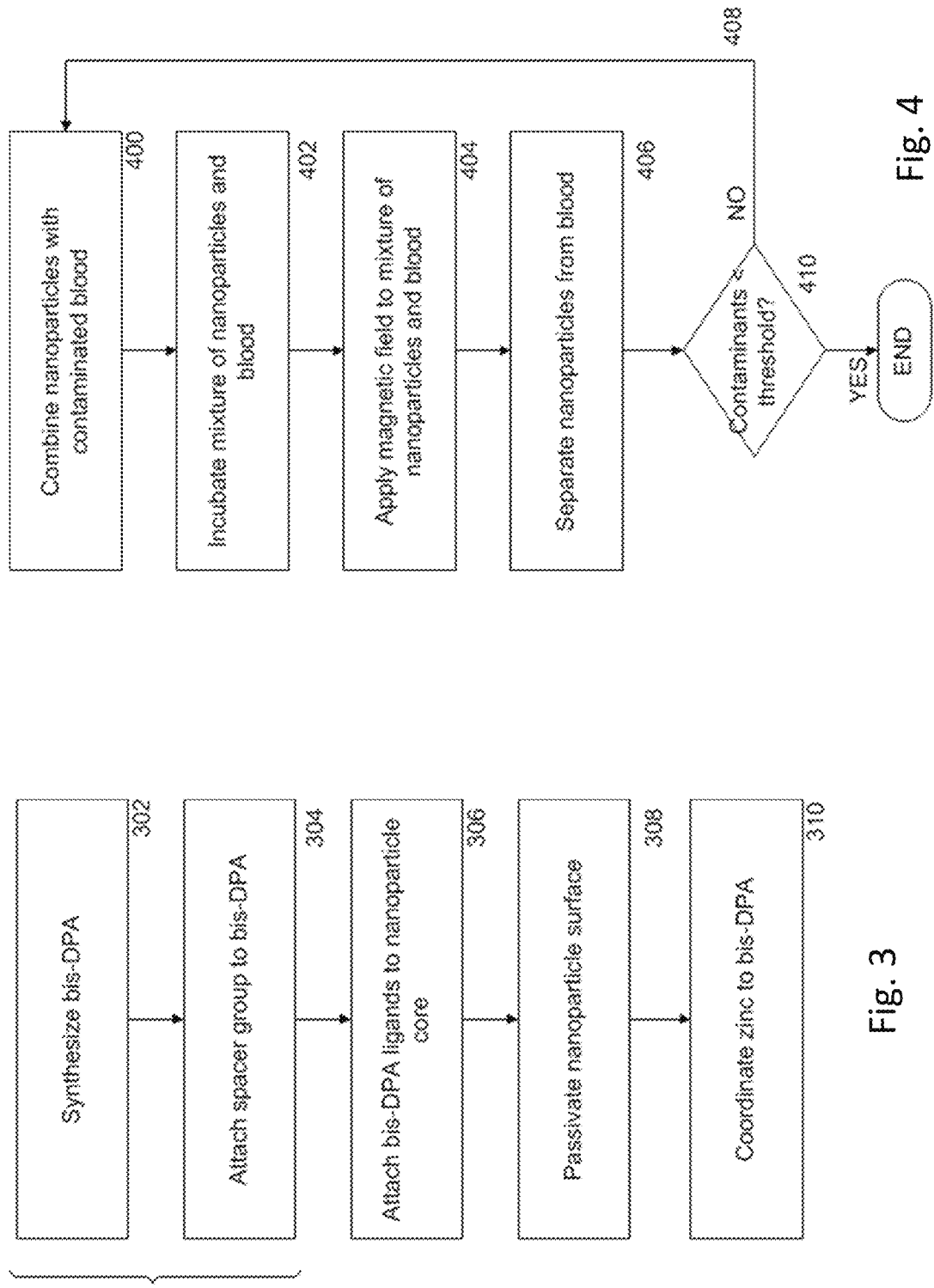

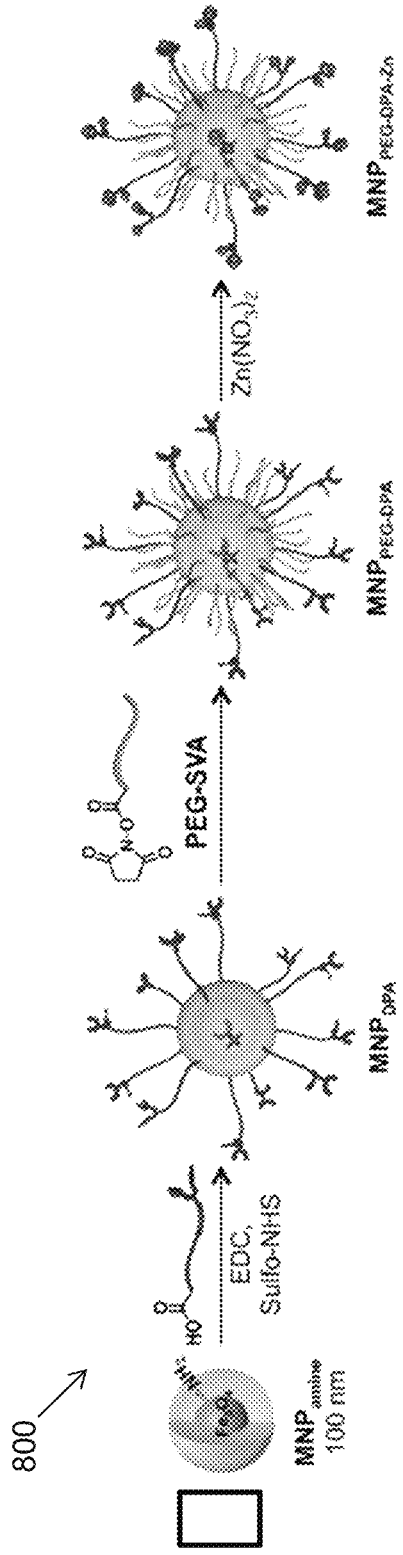
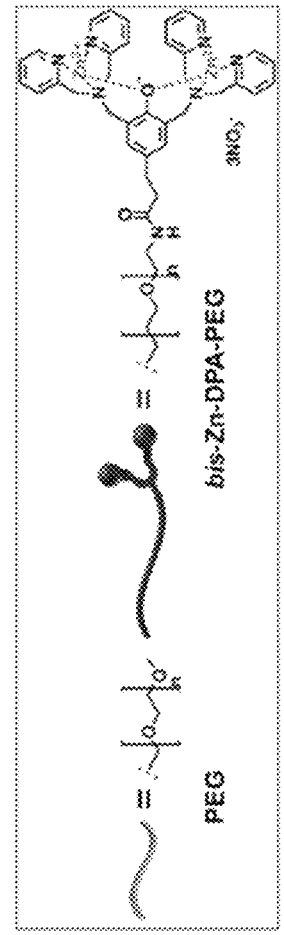
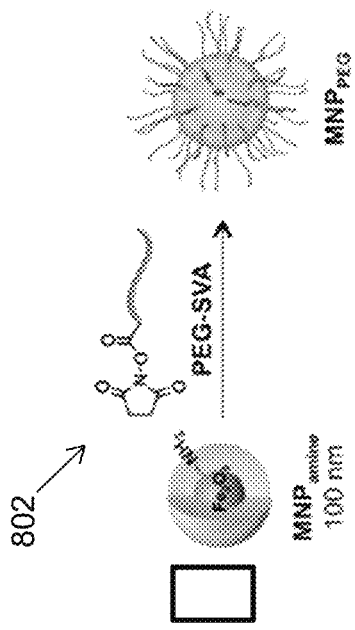
Fig. 8A
Fig. 8B

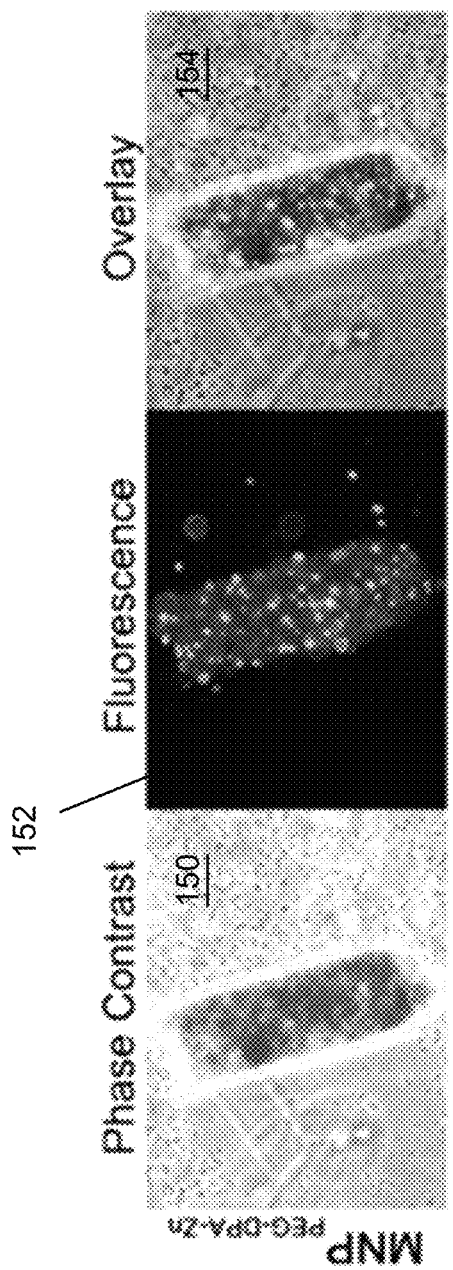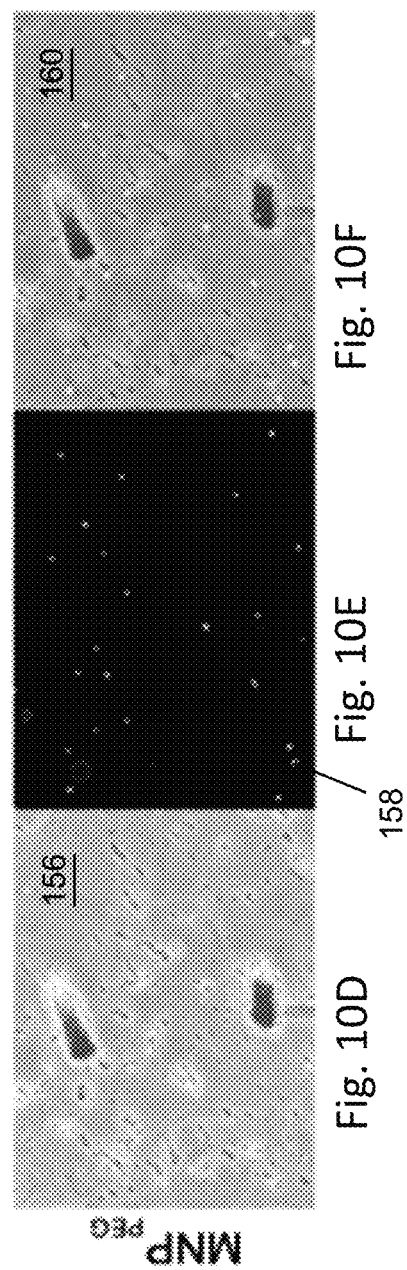

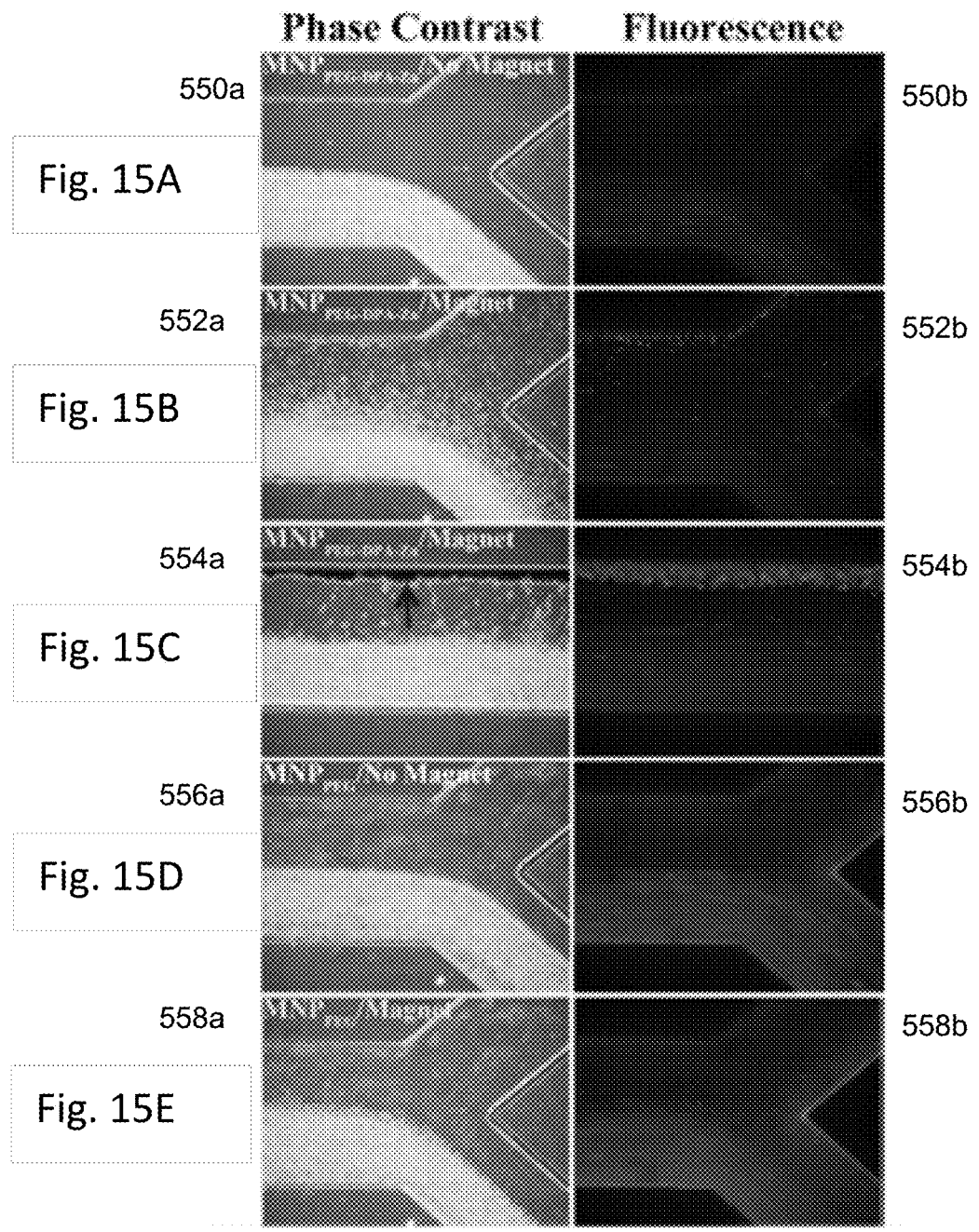

MAGNETIC SEPARATION USING NANOPARTICLES

CLAIM OF PRIORITY

This application is a continuation application of U.S. application Ser. No. 14/167,773, filed on Jan. 29, 2014 and claims priority to U.S. Provisional Application Ser. No. 61/758,046, filed on Jan. 29, 2013, the entire contents of which are hereby incorporated by reference.

FIELD OF THE INVENTION

The invention relates to magnetic separation, e.g., of bacteria and endotoxins, using nanoparticles.

BACKGROUND OF THE INVENTION

Bacterial sepsis is a serious clinical condition that can lead to multiple organ dysfunction and death despite timely treatment with antibiotics and fluid resuscitation. Gram-negative bacteria are common causative pathogens in bacterial sepsis. Common treatments for sepsis and septic shock include antibiotics, fluid resuscitation, and vasoactive medications. Other approaches, such as extracorporeal removal of inflammatory mediators, corticosteroids, and recombinant protein drug therapies have been introduced as experimental adjunct treatments. Antibody-based methods of separating bacteria from blood have also been developed.

SUMMARY OF THE INVENTION

The invention is based, at least in part, on the discovery that nanoparticles, such as magnetic nanoparticles, modified with ligands including metal ion-coordinated bis(dipicolylamine) (e.g., zinc ion-coordinated bis-Zn-DPA or copper ion-coordinated bis-Cu-DPA)(collectively, bis-M-DPA), can be utilized for highly selective and rapid separation of bacterial contaminants, such as bacteria, e.g., *E. coli*, and endotoxin, from liquids, such as blood, e.g., whole or diluted blood or serum, buffer solutions, albumin solutions, beverages for human and/or animal consumption, e.g., drinking water, liquid medications for humans and/or animals, or other liquids.

When bis-M-DPA modified nanoparticles are mixed with the liquid, e.g., blood, rapid binding occurs between the bis-M-DPA ligands on one or more nanoparticles and bacterial contaminants in the liquid. A motive force, e.g., a magnetic force, or other means of separation, e.g., size-based separation, centrifugal force separation, or flow cytometry-based separation, can then be applied to the nanoparticles to separate them from the liquid. Some of the nanoparticles have bacteria or endotoxin bound thereto, and when the nanoparticles are removed, the contaminants are also removed with them from the liquid. Microfluidic systems can be used as platforms for nanoparticle-based separations, providing a mechanism for efficient and selective separation of contaminants from liquids of any kind.

In one general aspect, nanoparticles are configured to bind to one or more bacterial contaminants. The nanoparticles include a core comprising or consisting of a magnetic material; and a plurality of ligands attached to the core. The ligands include bis(dipicolylamine) coordinated with a metal ion, e.g., $Zn^{2+}$ or $Cu^{2+}$ (bis-M-DPA), which can bind to the bacterial contaminant.

Various embodiments of these compositions can include one or more of the following features. The bis-M-DPA can be attached to the core via a spacer molecule having a molecular weight of 10 kDa to 50 kDa, e.g., 15, 20, 25, 30, 35, 40, or 45 kDa. In some cases, the spacer molecule can be a polymer spacer comprising or consisting of polyethylene glycol (PEG). The ligands can further include a filler molecule attached to the core. In some cases, the filler molecule can include or consist of PEG. The core can include one or more of a ferrimagnetic material, a ferromagnetic material, an antiferromagnetic material, a paramagnetic material, and a superparamagnetic material. In some cases, the core includes or consists of iron oxide, e.g., $Fe_3O_4$. An external surface of the core can also include or consist of a chemical group that can bind to the ligands.

In some embodiments, the diameter of the core can be about 50 to 250 nm, e.g., 60, 70, 80, 90, or 100 nm.

The nanoparticles can be configured such that binding between the nanoparticles and the bacterial contaminant can be substantially complete, e.g., 90% of the nanoparticles are bound to bacteria, within an incubation time of about five minutes or less, e.g., about one, two, three, or four minutes or less.

The bacterial contaminants can be or include Gram positive bacteria, Gram negative bacteria, and/or bacterial endotoxins.

In another general aspect, methods of separating bacterial contaminants from a liquid include combining the liquid with a plurality of nanoparticles that can bind to the bacterial contaminants. Each nanoparticle includes a core including a magnetic material and a plurality of ligands attached to the core. The ligands include bis(dipicolylamine) coordinated with $Zn^{2+}$ or $Cu^{2+}$ (bis-M-DPA). The methods further include applying a magnetic field to the liquid including the nanoparticles such that at least some of the nanoparticles are attracted by the magnetic field. The methods further include separating the liquid from the attracted nanoparticles. At least some of the bacterial contaminants, if present in the liquid, are bound to at least some of the attracted nanoparticles.

Various embodiments of these methods can include one or more of the following features. The bacterial contaminants can be or include Gram positive bacteria, Gram negative bacteria, and/or bacterial endotoxins. The liquid can be or include blood. The methods can further include directing the liquid including the nanoparticles through a flow channel. In some cases, applying a magnetic field includes applying a magnetic field across the flow channel. In some embodiments, separating the liquid includes allowing the liquid to exit the flow channel, and wherein the attracted nanoparticles remain in the flow channel. In some cases, directing the liquid through the flow channel includes flowing the liquid through the flow channel with a flow rate of at least about 5, 6, 7, 8, 9, or 10 mL/hour, or much faster, e.g., at least 40, 50, 60, or 70 mL/hour. In some cases, the methods further include directing the liquid including the nanoparticles through a plurality of flow channels. Applying a magnetic field can include applying a magnetic field across each of the plurality of flow channels.

The methods can further include incubating the liquid including the nanoparticles prior to applying the magnetic field. In some cases, incubating the liquid including the nanoparticles includes incubating for about five minutes or less, e.g., about one, two, three, or four minutes or less, to achieve substantially complete binding between the nanoparticles and the bacterial contaminant.

In another general aspect, systems for separating one or more bacterial contaminants from a liquid include a plurality of nanoparticles that can bind to the target species. Each nanoparticle includes a core comprising a magnetic material, and a plurality of ligands attached to the core. The ligands include bis(dipicolylamine) coordinated with a metal, e.g., $Zn^{2+}$ or $Cu^{2+}$ (bis-M-DPA). The systems further include a source of a magnetic field arranged to apply the magnetic field to a liquid including the plurality of nanoparticles. At least some of the nanoparticles are attracted by the magnetic field. The system further includes a flow path for separating the liquid from the attracted nanoparticles. Some of the bacterial contaminants, if present in the liquid, are bound to at least some of the attracted nanoparticles.

Different embodiments of these systems can include one or more of the following features. The systems can further include a flow channel configured to receive the liquid including the nanoparticles. In some cases, the magnet is disposed to a side of the flow channel and configured to apply the magnetic field across the flow channel. In some cases, the flow path includes an exit from the flow channel, and wherein the attracted nanoparticles remain in the flow channel. In some cases, the system further includes a plurality of flow channels configured to receive the liquid including the nanoparticles.

The nanoparticles can be configured such that binding between the nanoparticles and the bacterial contaminants can be substantially complete within an incubation time of about five minutes or less, e.g., about one minute or less. The bacterial contaminants include Gram positive bacteria, Gram negative bacteria, and/or bacterial endotoxins. The liquid can be or include blood.

The term "bacterial contaminants" refers to bacteria and endotoxins of any species and a liquid may contain any type of bacteria, or multiple types of bacteria, or only endotoxins, or both bacteria and endotoxins.

The approaches described herein for bacterial contaminant removal, e.g., magnetic separation, from fluids have several advantages. For instance, magnetic separation using nanoparticles is generic and can be used on many target bacterial contaminant species, including Gram positive bacteria, Gram negative bacteria, and/or bacterial endotoxins. Separation using nanoparticles is also highly selective; the nanoparticles have negligible affinity toward normal mammalian cells and other materials that may be present in the fluids. Binding between nanoparticles and a target species is rapid and very short incubation times can be used. In addition, separation can be achieved at rapid flow rates through microfluidic systems, enabling efficient separation of bacterial contaminants from fluids. The synthetic ligands used are inexpensive and straightforward to synthesize, can be easily conjugated to nanoparticles, and are stable against denaturation at room temperature and even at body temperature.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 3 is a flow chart of a process for making nanoparticles.
FIG. 4 is a flow chart of a process for magnetic separation.
FIGS. 8A and 8B are schemes for the modification of magnetic nanoparticles with ligand molecules.
FIG. 10A-10F are phase contrast, green fluorescent, and overlay images of nanoparticles and *E. coli*.
FIGS. 15A-15E are phase contrast and green fluorescent images of nanoparticles and *E. coli* in a dual inlet microfluidic system.

DETAILED DESCRIPTION

Figure 1:
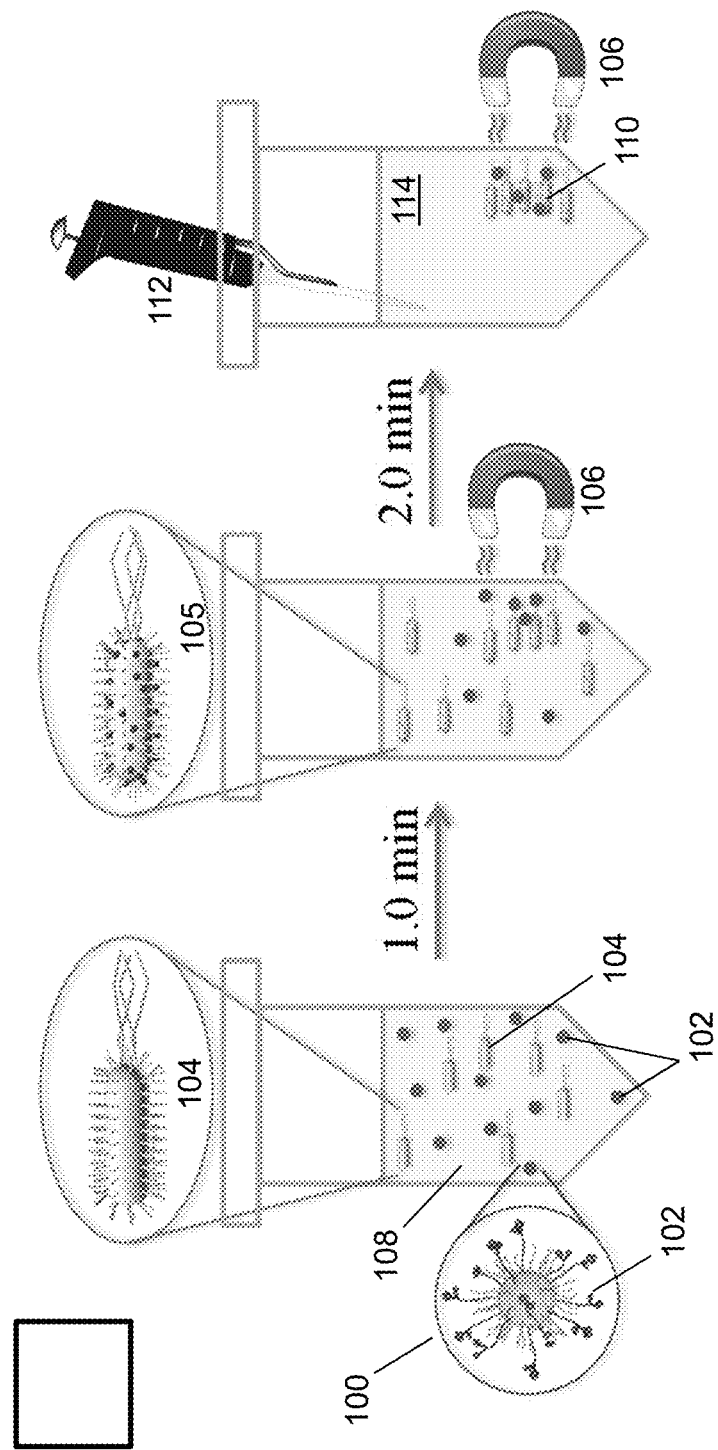
FIG. 1 is a diagram of a nanoparticle binding to a bacterial cell.

Referring to FIG. 1, nanoparticles, e.g., magnetic nanoparticles 100 modified with ligands 102 including metal-coordinated bis(dipicolylamine) (e.g., bis-Zn-DPA or bis-Cu-DPA) (referred to collectively herein as "bis-M-DPA") can be utilized for highly selective and rapid separation of bacterial contaminants such as bacteria 104, e.g., *E. coli*, and endotoxins, from liquids such as whole blood, buffers, albumin, and other liquids. When nanoparticles 100 are mixed with blood, rapid binding (e.g., within about one minute or less) occurs between the bis-M-DPA ligands on one or more nanoparticles 100 and the target bacteria 104 or endotoxin, forming nanoparticle-contaminant complexes 105. If the nanoparticles are magnetic or include a magnetic material, a magnetic field applied to the blood attracts nanoparticles 100, some of which have bacteria or endotoxin bound thereto, thus reducing the concentration of bacterial contaminants in the blood. Stationary magnetic separation with a magnet 106 can be used to separate bacterial contaminants bound to nanoparticles from the liquid. Microfluidic systems can also be used as a platform for nanoparticle-based magnetic separations.

In other implementations, the nanoparticles bound to the bacterial contaminants are designed to be a size that of can be separated from the fluid using a microfluidic system, e.g., as described in U.S. Pat. No. 8,304,230, which separates the particles based on size. Alternatively, the nanoparticles bound to the bacterial contaminants can be removed from the fluid using centrifugation or sedimentation. In other implementations, microparticles can be used to bind bacterial contaminants.

Nanoparticle Compositions and Synthesis

Figure 2B:
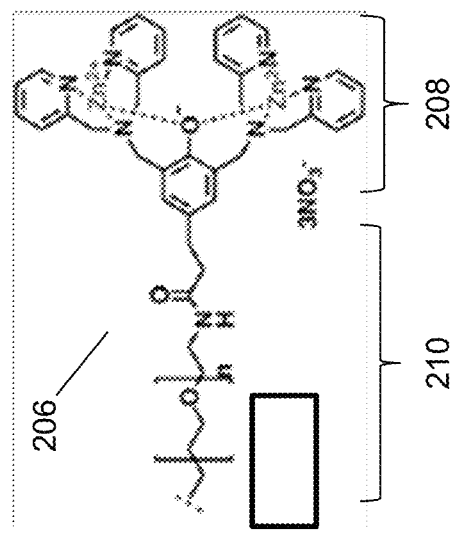
FIG. 2B is a diagram of an active ligand molecule.
Figure 2A:
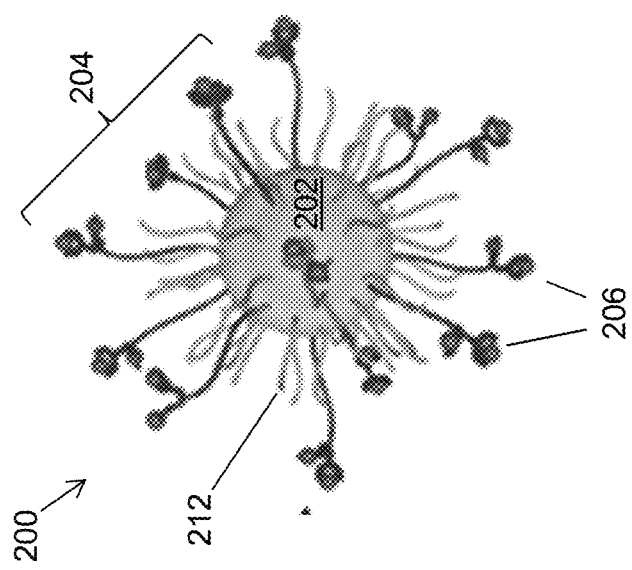
FIG. 2A is a diagram of a nanoparticle.

Referring to FIG. 2A, magnetic nanoparticles 200 include a magnetic core 202 and ligand molecules 204. In general, the core is formed of a magnetically susceptible material. For instance, the core 202 can be a ferrimagnetic material such as, e.g., iron oxide ($Fe_3O_4$), or another ferrimagnetic material. The core 202 can also be an antiferromagnetic material, such as, e.g., chromium oxide ($Cr_2O_3$). The core 202 can also be a paramagnetic material, such as, e.g., lanthanide oxide, manganese oxide, or another paramagnetic material. The core 202 can also be a superparamagnetic material, such as, e.g., iron oxide ($Fe_2O_3$). The core 202 can also be a ferromagnetic material, such as, e.g., nickel, cobalt, alnico (an aluminum-nickel-cobalt alloy of iron, or another ferromagnetic material. In some implementations, the nanoparticles can be cross-linked iron nanoparticles or monocrystalline iron nanoparticles, such as those described in U.S. Patent Pub. 2009/0029392, the contents of which are incorporated herein by reference. In some examples, the outer surface of the core 202 can include chemical groups that are capable of binding to the ligand molecules 204. For instance, the outer surface of the core 202 can include carboxylic acids, amines, thiols, bromoacetyl compounds, alcohols, or another chemical group.

The ligand molecules 204 include active ligand molecules 206 that are capable of binding to the target bacterial contaminant species, such as Gram-positive bacteria, Gram-negative bacteria, and endotoxins. For instance, the active ligand molecules can include zinc-coordinated bis(dipicolylamine) (bis-Zn-DPA) 208, copper-coordinated DPA (bis-Cu-DPA), other another molecule. Bis-M-DPA forms coordination bonds with anionic phospholipids, which are present at high density on the outer membrane of Gram-positive and Gram-negative bacterial cells. Furthermore, the bis-M-DPA coordination complex with anionic phospholipids provides negligible affinity toward normal mammalian cells such as red blood cells or white blood cells or toward negatively charged proteins such as albumin. Bis-M-DPA is thus capable of highly selective binding to Gram-positive bacteria, Gram-negative bacteria, and endotoxin with little to no binding to normal cells and proteins.

Referring also to FIG. 2B, in one example of an active ligand module 206, bis-Zn-DPA can be attached to the nanoparticles 200 via a spacer group 210. The spacer group 210 provides space between the core 202 and bis-Zn-DPA 208 to avoid crowding among the bulky bis-Zn-DPA groups and to enhance the molecular mobility of the bis-Zn-DPA groups. The spacer group 210 can be a polymer, such as polyethylene, polyethylene glycol (PEG), polypropylene, or another polymer. In one example, PEG with a molecular weight (MW) of about 3.5, 5.0, 10, 15, 20, 25, 40, or 50 kDa can be used as the spacer group 210. The spacer group 210 is terminated with an end group capable of binding to the core 202 or to the chemical groups 206 on the outer surface of the core 202. For instance, the end group can be, e.g., a carboxylic acid (e.g., capable of binding to a surface amine via carbodiimide chemistry), an amine (e.g., capable of binding to a surface carboxylic acid via carbodiimide chemistry), a thiol (e.g., capable of binding to a surface thiol via a disulfide bond or via reaction with a maleimide), a bromoacetyl compound (e.g., capable of binding to a surface via a nucleophilic addition), alcohol (capable of binding to a surface via silane chemistry), or another end group. In some examples, there can be about 2,500 active ligand molecules 206 per 100 nm diameter nanoparticle 200, e.g., as characterized in (Sofia, S. J., Premnath, V., Merill, E. W., 1998. Poly(ethylene oxide) grafted to silicon: grafting density and protein adsorption. Macromolecules 31, 5059-5070), the contents of which are incorporated herein by reference.

The ligand molecules 204 can also include filler molecules 212 that passivate binding sites on the core 202 (e.g., chemical groups on the outer surface of the core) to which a bis-Zn-DPA ligand is not bound, thus preventing non-specific binding to those unreacted binding sites. The filler molecules 212 can be polymers, such as, e.g., polyethylene, PEG, polypropylene, or another polymer. Each filler molecule 212 is terminated with an end group capable of binding to the core 202 (e.g., to the chemical groups on the surface of the core). For instance, the end group can be, e.g., a carboxylic acid, a thiol, an amine, or another end group.

In one example, a $Fe_3O_4$ core 202 includes amines on its outer surface. The active ligand molecules 206 are formed of bis-Zn-DPA with a carboxylic acid-terminated PEG spacer. This example of a ligand composition is referred to herein as bis-DPA-PEG-COOH. The filler molecules 212 are carboxylic acid-terminated PEG. Bis-DPA-PEG-COOH is capable of rapid binding to Gram positive and Gram negative bacteria and to endotoxin. In addition, bis-DPA-PEG-COOH is stable at room temperature and thus has a long shelf life, and is also stable at body temperature and thus well suited to use in clinical applications.

The size of the core 202 is generally less than about several micrometers, e.g., about 100 nm or less. In some examples, the minimum core size may be limited by the size of the magnetic moment of the nanoparticle, e.g., depending on the strength of the magnet used for magnetic separation. A smaller core provides a larger surface area to volume ratio and thus can provide better performance in clinical applications (e.g., more rapid binding to the target species). In some examples, reducing the size of the core 202 below a threshold size can reduce the magnetic moment of the core, thus reducing the ability of the nanoparticles to respond to a magnetic field. For instance, for $Fe_3O_4$ nanoparticles, the magnetic moment of the core begins to decrease for core sizes less than about 50 nm.

FIG. 3 is a flowchart showing a process for synthesizing the nanoparticles of FIG. 2. Ligand molecules including bis-DPA (referred to herein as "bis-DPA ligands") are synthesized (300) by synthesizing 3-(3,5-bis((bis(pyridin-2-ylmethyl)amino)methyl)-4-hydroxyphenyl) propanoic acid (bis-DPA) (302) and attaching a spacer group (304). For instance, bis-DPA can be synthesized by a solution-phase preparation of methyl 3-(3,5-bis((bis(pyridin-2-ylmethyl)amino)methyl)-4-hydroxyphenyl)propanoate, bis-DPA-methyl ester (bis-DPA-ME) and the conversion of bis-DPA-ME into bis-DPA. A spacer group (e.g., PEG) terminated with an end group (e.g., COOH) can be attached to bis-DPA through any of a variety of chemical reactions. For instance, carbodiimide chemistry can be used to form bis-DPA-PEG-COOH through the reaction of bis-DPA and NH2-PEG-COOH in the presence of 1-ethyl-3-(3-dimethylaminopropyl)-carbodiimide hydrochloride (EDC) and N-hydroxysuccinimide (NHS).

Bis-DPA ligands (e.g., PEG-DPA) are attached to the nanoparticle cores (306) via any number of standard chemical reactions between the end groups of the ligands (e.g., COOH) and the chemical groups on the outer surface of the nanoparticle cores using standard techniquires. For instance, carbodiimide chemistry can be used to attach PEG-DPA to amine-terminated $Fe_3O_4$ nanoparticles through the reaction of PEG-DPA and the nanoparticles in the presence of EDC and NHS. Other chemistries can also be used, e.g., based on the identity of the ligand end groups and the chemical groups on the surface of the nanoparticles.

Unreacted chemical groups on the surface of the nanoparticles are passivated (308) with filler molecules. For instance, PEG-succinimidyl valerate (PEG-SVA) can be used to passivate the nanoparticle surface by reacting PEG-SVA with amine-terminated $Fe_3O_4$ nanoparticles. Other chemistries can also be used, e.g., based on the chemical groups on the surface of the nanoparticles.

Zinc (e.g., $Zn^{2+}$) is coordinated to the bis-DPA groups on the nanoparticles (310) to create bis-Zn-DPA-PEG modified nanoparticles (referred to herein as $NP_{PEG-DPA-Zn}$). For instance, zinc can be coordinated to bis-DPA by stirring a solution of nanoparticles in the presence of a zinc compound, such as zinc nitrate hexahydrate. In another example, copper (e.g., $Cu^{2+}$) can be coordinated to the bis-DPA groups on the nanoparticles to create bis-Cu-DPA-PEG modified nanoparticles. In another example, bis-Cu-DPA-PEG can be directly attached to the nanoparticle cores.

The resulting nanoparticles include active ligands including, e.g., bis-Zn-DPA (e.g., bis-Zn-DPA-PEG) or bis-Cu-DPA (e.g., bis-Cu-DPA-PEG) capable of binding to target species, such as Gram-positive bacteria, Gram-negative bacteria, and endotoxins; and filler molecules (e.g., PEG-SVA). These nanoparticles are referred to herein as $NP_{DPA-Zn}$ (e.g., $NP_{PEG-DPA-Zn}$) or $NP_{DPA-Cu}$, or collectively as $NP_{DPA-M}$.

Magnetic Separation of Bacterial Contaminants

Referring to FIG. 4, magnetophoresis can be used to clear bacterial contaminants such as Gram-positive bacteria, Gram-negative bacteria, and endotoxins, from liquids such as blood using $NP_{DPA-M}$. Referring also to FIG. 1, for example, $NP_{DPA-M}$ 100 are combined (400) with a contaminated sample of blood 108 and incubated (402) to allow binding between bis-M-DPA and contaminants 104 in the blood 108. In some examples, multiple nanoparticles 100 bind to a single contaminant 104 (e.g., a single bacterial cell). The concentration of nanoparticles in the blood can be from about $1.0 \times 10^4$/mL to about $1.0 \times 10^{12}$/mL, e.g., about $1.0 \times 10^{11}$/mL.

The binding kinetics between bis-M-DPA on nanoparticles and blood contaminants are rapid. For instance, incubation times less than five minutes (e.g., less than one minute) can be sufficient for binding to be substantially complete, e.g., such that a further increase in incubation time may not cause a further increase in binding. Without being bound by theory, it is believed that this rapid binding rate can be attributable to the high mobility of nanoparticles, which can increase the probability of an encounter between a nanoparticle and a contaminant; and/or the high surface area to volume ratio of nanoparticles, which can increase the ligand loading capacity of the nanoparticles. The rapid binding rate can also be attributed to the presence of spacer groups of the appropriate length (e.g., between about 1.0 and 20 kDa), such as PEG spacers, that enhance the molecular mobility of the bis-M-DPA groups on the ligand molecules and the surface of the nanoparticles.

After incubation, a magnetic field is applied (404) to the mixture of blood 108 and nanoparticles 100. For instance, a magnet 106 or an electromagnet can be used to apply a magnetic field to the mixture. The magnetic nanoparticles 100 move relative to the blood 108. For instance, the nanoparticles 100 can move toward the magnet 106. Contaminants 104 that are bound to the nanoparticles 100 are also moved along with the nanoparticles 100, e.g., toward the magnet 106. In the example depicted in FIG. 5B, one nanoparticle 100 is shown binding to each contaminant 104. In some examples, multiple nanoparticles 100 can bind to each contaminant 104.

The attracted nanoparticles 100, some of which have contaminants 104 bound thereto, are separated (406) from the blood 108. For instance, in the example of FIG. 1, a stationary magnetic separation is carried out, creating an accumulation 110 of nanoparticles, from which decontaminant blood 114 can be decanted, e.g., with a syringe 112. In other exampes, magnetic separation can occur in a flow cell such that the blood 108 flows past the separated nanoparticles 100 and exits the flow cell.

In some examples, the magnetic separation process is repeated (408), using fresh nanoparticles for each iteration of the process. For instance, the magnetic separation process can be repeated a fixed number of times (e.g., two times, three times, or another number of times). The magnetic separation process can also be repeated based on the results of a test, e.g., indicative of a level of contaminants in the blood. For instance, the magnetic separation process can be repeated until the level of contaminants falls below a threshold level (410).

In some examples, centrifugation can be used to remove nanoparticles bound to contaminants.

Microfluidic Systems for Magnetic Separation

Magnetic separation of contaminants from blood using $NP_{DPA-M}$ can be achieved with microfluidic systems. Microfluidic technologies are often well-suited to the separation and sorting of cells under continuous fluid flow. In a system for microfluidic magnetic separation of contaminants, a mixture of blood and $NP_{DPA-M}$ is injected into an inlet of a microfluidic system. A magnet, e.g., a permanent magnet or electromagnet, along the flow path through the system applies a magnetic field to the blood within the system, attracting the nanoparticles with bound contaminants and preventing them from flowing to the outlet of the system with the blood.

In other implementations, other forces and techniques can be used to remove the nanoparticles bound to bacterial contaminants from the liquid sample. For example, the nanoparticles can be bound to reporter groups, e.g., fluorescent molecules, which can be used to selectively separate the marked nanoparticles from the fluid, e.g., using flow cytometry or optical forces using standard techniques. Other methods based on size-separation techniques can also be used. For example, the nanoparticles can be bound to particles of a certain size and then passed through a microfluidic size-separation device known in the field.

Figure 5:
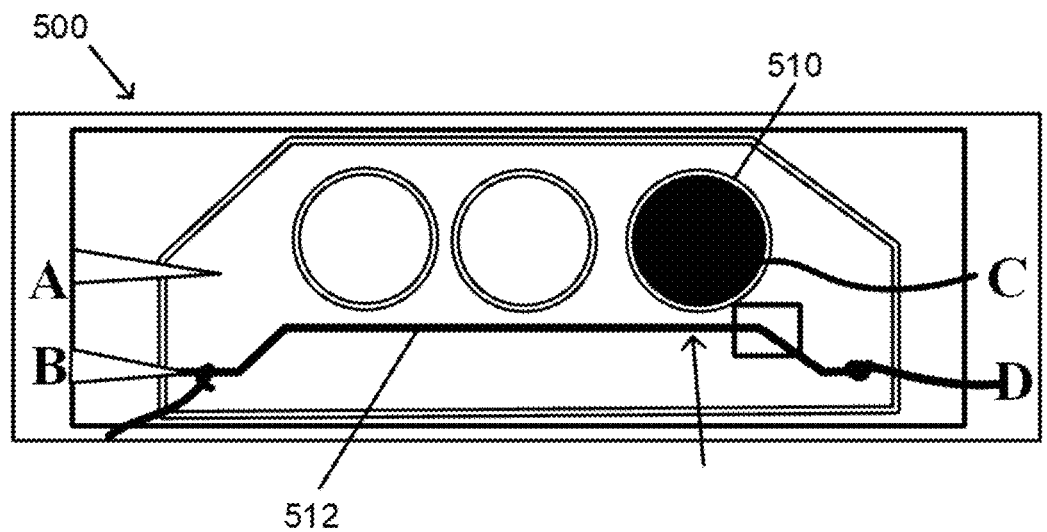
FIG. 5 is a diagram of a dual-inlet microfluidic system.

Referring to FIG. 5, in one implementation, a dual inlet microfluidic system 500 includes two inlets (inlet A and inlet B) and two outlets (outlet C and outlet D). One or more magnets 510 are positioned along a common flow channel 512 between the inlets A and B and the outlets C and D to apply a magnetic field to the liquid within the system 500.

In one example, saline is injected into inlet A and a liquid mixture of $NP_{DPA-M}$ and contaminants such as E. coli (e.g., as whole blood or in a buffer such as phosphate buffered saline (PBS) is injected into inlet B. In the absence of a magnetic field and at a sufficiently low flow rate (e.g., about 9.0 mL/hour or less), convective mixing between two interfacing parallel flows was negligible and flow through the common flow channel 512 is laminar. Thus, in the absence of a magnetic field, nanoparticles, contaminants, and any other components of the liquid mixture entering the flow channel 512 from inlet B will exit through outlet D. The saline solution exiting through outlet C will contain little or no nanoparticles or contaminants. In the presence of a magnetic field, nanoparticles are drawn into the saline flow and exit through outlet C, bringing along any contaminants bound thereto. The liquid exiting through outlet D is thus relatively more free of contaminants than was the liquid entering into inlet B. In some implementations, the liquid can be run through the system again to further reduce the level of bacterial contaminants.

Figure 6:
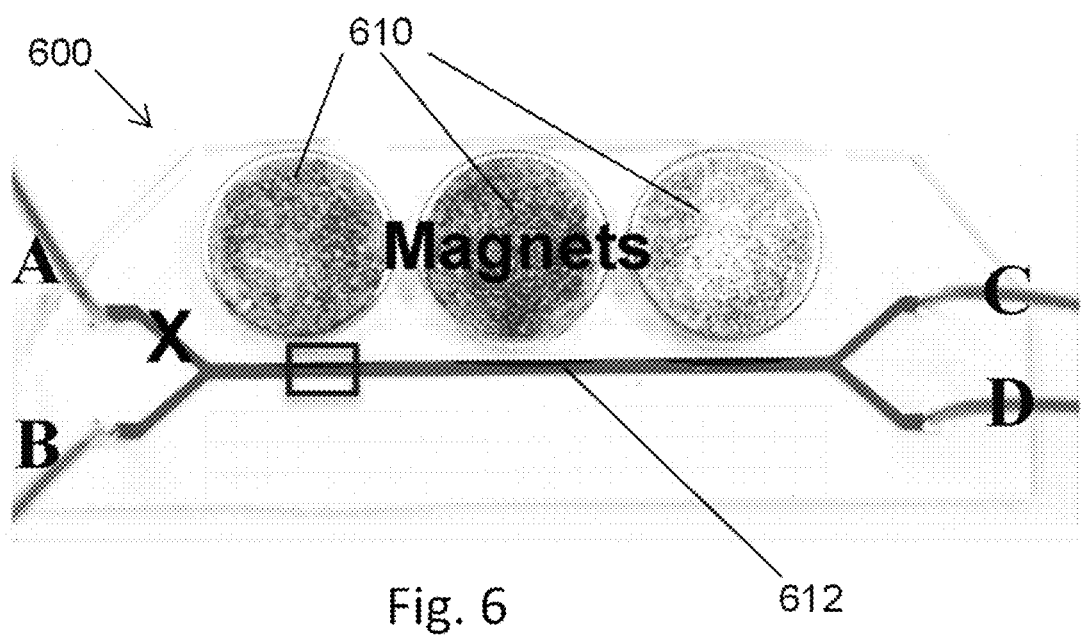
FIG. 6 is a diagram of a single-inlet microfluidic system.

Referring to FIG. 6, in another implementation, a single inlet microfluidic system 600 includes a single inlet (inlet B) and two outlets (outlet C and outlet D). One or more magnets 610 are positioned along a common flow channel 612 between inlet B and outlets C and D to apply a magnetic field to the liquid within the system 600. A liquid mixture of $NP_{DPA-M}$ and contaminants (e.g., as whole blood or in a buffer such as PBS) is injected into inlet B. Separation of contaminants from blood is effected by the accumulation of $NP_{DPA-M}$ at the walls of the common flow channel 612 adjacent to the magnets 610, instead of by removal through one of the two outlets. The liquid exiting through both outlet C and outlet D is thus relatively more free of contaminants than was the liquid entering into inlet B.

A system of nested or multiplexed microfluidic devices can enhance the separation efficiency by allowing multiple magnetic separations to be completed in a single pass through the system. Individual single inlet microfluidic systems (e.g., such as system 600) can be connected in various combinations, such as in series, in parallel, or both, to provide a desired number of magnetic separations per pass through the system.

Figure 7:
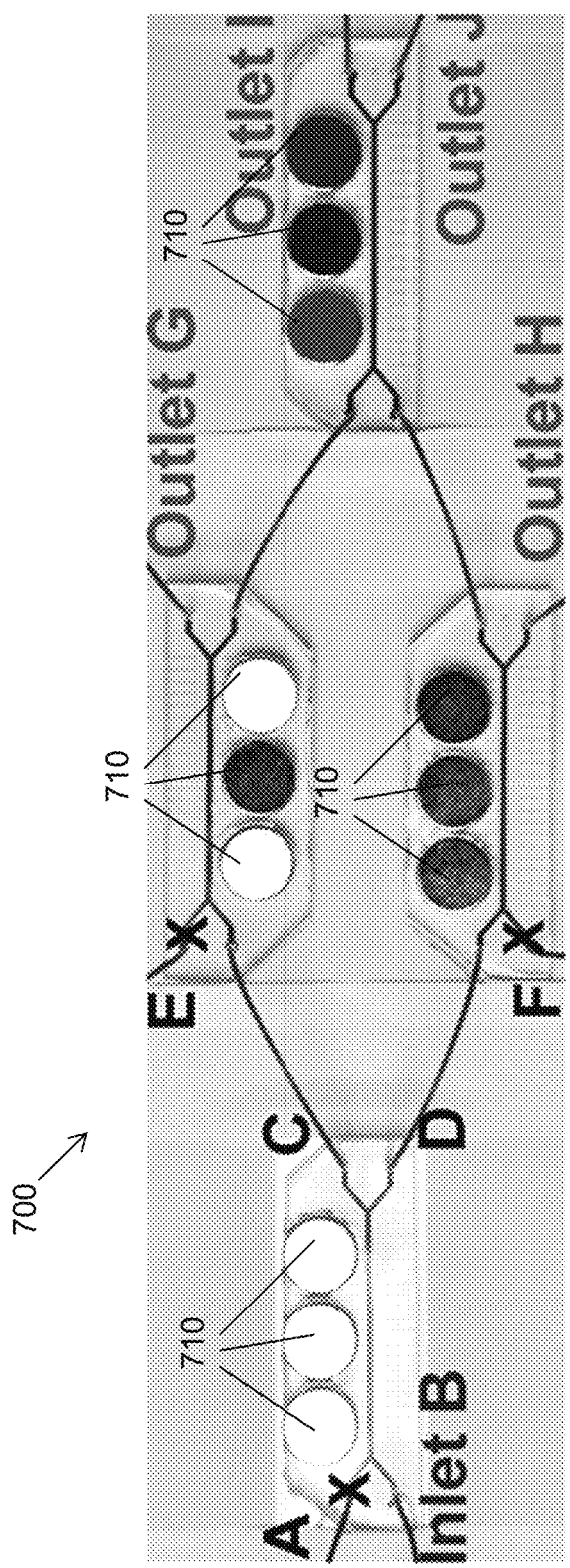
FIG. 7 is a diagram of a networked microfluidic system.

Referring to FIG. 7, in another implementation, a nested system 700 includes four individual single inlet microfluidic systems 600. Inlets A, E, and F were closed so that inlet B was the only inlet into the nested system 700. A liquid mixture of $NP_{DPA-M}$ and contaminants (e.g., as whole blood or in a buffer such as PBS) is injected into the single inlet B. Liquid exits at outlets G and H after passing through two magnetic separations effected by magnets 710 and thus has a concentration of contaminants that is less than the concentration of the injected liquid. Liquid exits at outlets I and J after passing through three magnetic separations and thus has a concentration of contaminants that is less than the concentration of contaminants in the liquid that exits at outlets G and H. In some examples, significant reductions in the concentration of contaminants (e.g., reductions of at least about 80%, or at least about 95%) can be achieved by the example nested system 700.

Magnetic separation using a microfluidic system, such as a single inlet microfluidic system, can be achieved at high flow rates of liquid through the system. For example, contaminants can be separated from liquid with a flow rate of at least about 9 mL/hour (e.g., at least about 18 mL/hour, at least about 30 mL/hour, or at least about 60 mL/hour).

Applications for Magnetic Separation Using Nanoparticles

The short incubation time for binding contaminants to $NP_{DPA-M}$ and the ability to use high flow rates through microfluidic systems render the use of $NP_{DPA-M}$ to separate contaminants from liquids such as blood make the new methods described herein well-suited for clinical applications. Minimizing the time that blood spends outside the body during decontamination reduces the risk of coagulation and the risk of infection. Furthermore, the present nanoparticle-based approach to separating bacterial contaminants from blood is compatible with existing blood-modifying technology used in intensive care units, such as pheresis, dialysis, and Extracorporeal Membrane Oxygenation (ECMO).

Sepsis is a highly lethal condition that frequently arises from the presence of bacteria in the bloodstream. While bacteremia is an important component of the pathogenesis of sepsis, the release of endotoxins from bacteria is a major causative factor in septic shock. The new methods described herein provide an efficient mechanism for clearing Gram-negative bacteria, such as *E. coli*, endotoxins, and other bacterial contaminants from the bloodstream of septic patients.

To further improve the efficiency of the nanoparticle-based approach described herein, the accumulation of nanoparticles near the magnets in microfluidic systems can be reduced. In some implementations, the accumulation of nanoparticles near the magnets can gradually reduce the efficiency of the magnetic separation, thus limiting the volume of blood that could be filtered before cleaning or replacing the microfluidic system. This potential problem can be addressed by employing stronger magnets, using an automated flushing system, e.g., a back-flushing system, to remove the accumulated nanoparticles, and/or increasing the contact area between the magnets and the flow channels to mitigate nanoparticle accumulation near the magnets. In addition, lower concentrations of nanoparticles can be used, and/or blood can be diluted prior to processing.

EXAMPLES

The invention is further described in the following examples, which do not limit the scope of the invention described in the claims.

The following examples generally show the synthesis and characterization of nanoparticles modified with bis-DPA-PEG-Zn. The examples further show the ability of these nanoparticles to magnetically separate *E. coli* and endotoxin from liquids and from whole blood. In addition, examples of microfluidic systems that can be used to implement the magnetic separation of *E. coli* and endotoxin from blood are demonstrated.

Example 1—Nanoparticle Synthesis and Characterization

FIG. 8A shows a scheme 800 for the preparation of magnetic nanoparticles modified with bis-DPA-PEG-Zn (referred to herein as $NP_{PEG-DPA-Zn}$). Bis-DPA with a PEG (MW=10 kDa) spacer (bis-DPA-PEG-COOH) was immobilized on the surface of 100 nm diameter amine-terminated $Fe_3O_4$ magnetic nanoparticles (approximately 300 amines per nanoparticle, SiMAG-Amine particles, chemicell GmbH, Berlin, Germany) through carbodiimide chemistry using EDC and (sulfo-NHS). Excess bis-DPA-PEG-COOH was activated by N-hydroxysulfosuccinimide (sulfo-NHS) with EDC (10-fold molar excess each) and added to a solution of nanoparticles. The nanoparticle solution was washed twice with carbonate buffer (50 mM sodium carbonate, pH 9.5) using a magnetic separator (MagnetoPURE, chemicell GmbH). After 2 hours of reaction at room temperature, the modified nanoparticles were washed twice with carbonated buffer.

Unreacted free amines on the surface of the nanoparticles were passivated with PEG-succinimidyl valerate (PEG-SVA). PEG-SVA (2.0 kDa, 10-fold molar excess, Laysan Bio, Inc., Arab, Ala.) was added to the nanoparticle solution and allowed to react for two hours. The nanoparticles were then washed twice with ddH2O to obtain nanoparticles modified with bis-DPA-PEG and PEG-SVA using a magnetic separator. $Zn^{2+}$ was coordinated to the bis-DPA to create bis-DPA-PEG-Zn modified nanoparticles ($NP_{PEG-DPA-Zn}$). Excess of zinc nitrate hexahydrate was added to the $NP_{PEG-DPA}$ solution and then the mixture was stirred for 30 minutes at room temperature. Excess of $Zn^{2+}$ was removed by magnetophoresis (3 times).

FIG. 8B shows a scheme 802 for the preparation of a control sample of magnetic nanoparticles modified with PEG-SVA (referred to herein as $NP_{PEG}$). $NP_{PEG}$ were prepared in the same manner as $NP_{PEG-DPA-Zn}$ but without the addition of the bis-DPA-PEG-COOH.

Carbodiimide chemistry on the modified nanoparticles was validated by measurements of the zeta potentials of the nanoparticles. The zeta potentials of the nanoparticles were measured at room temperature with a Delsa Nano C zeta potential instrument (Beckman Coulter, Brea, Calif.). Data given below are means±standard deviations. N=4 for all groups.

Referring to Table 1, a significant decrease in zeta potential was observed upon addition of PEG-SVA to a solution of unmodified nanoparticles (from 39 mV for unmodified nanoparticles to 12 mV for $NP_{PEG}$, $p<0.01$). When excess PEG-SVA was added to bis-DPA-modified nanoparticles ($NP_{DPA}$) to remove unreacted amines, the zeta potential decreased from 36 mV for $NP_{DPA}$ to 32 mV for $NP_{PEG-DPA}$ ($p<0.01$). These results validate the carbodiimide chemistry on the surface of the nanoparticles.

TABLE 1

| Zeta potential (mV) of Nanoparticles | | | | |
| --- | --- | --- | --- | --- |
| $NP_{amine}$ | $NP_{DPA}$ | $NP_{PEG-DPA}$ | $NP_{PEG-DPA-Zn}$ | $NP_{PEG}$ |
| 39.25 ± 0.67 | 36.00 ± 1.36 | 31.70 ± 1.64 | 33.22 ± 1.14 | 12.63 ± 0.96 |

The association of Zn with bis-DPA was demonstrated with energy dispersive X-ray spectroscopy (EDS) in a scanning electron microscope (SEM). SEM imaging was performed with a JEOL 5910 microscope (JEOL, Tokyo, Japan) equipped with a detector for EDS. Prior to SEM analysis of nanoparticles, nanoparticles were mixed with $Zn(NO_3)_2$, washed three times with deionized water to remove excess $Zn(NO_3)_2$, and freeze-dried. The nanoparticles aggregated during the freeze-drying process. The dried nanoparticles were placed on carbon double-sided tape. Imaging was performed with 20 kV acceleration voltage.

Figure 9A:
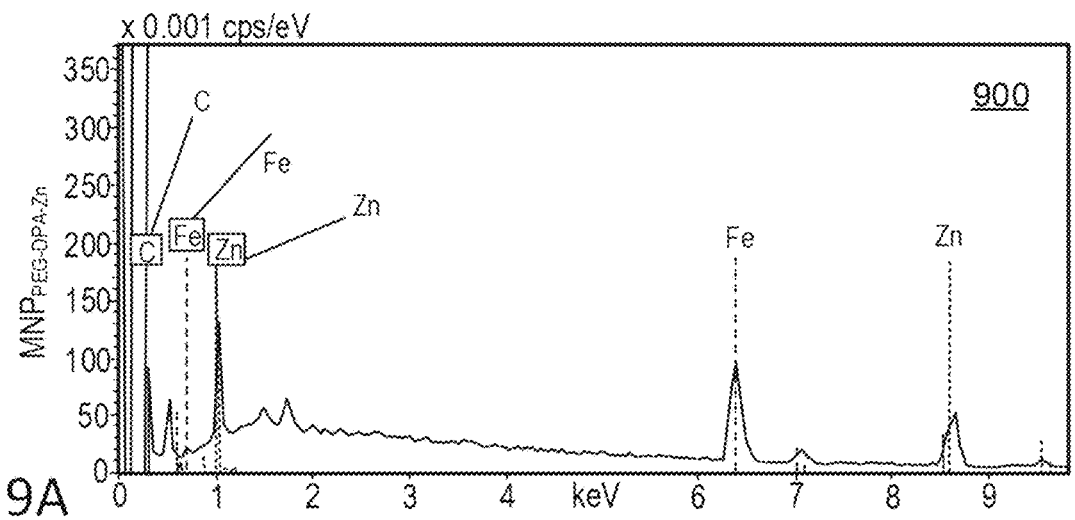
FIGS. 9A-9C are energy dispersive X-ray spectra for nanoparticles of various compositions mixed with a zinc compound.
Figure 9B:
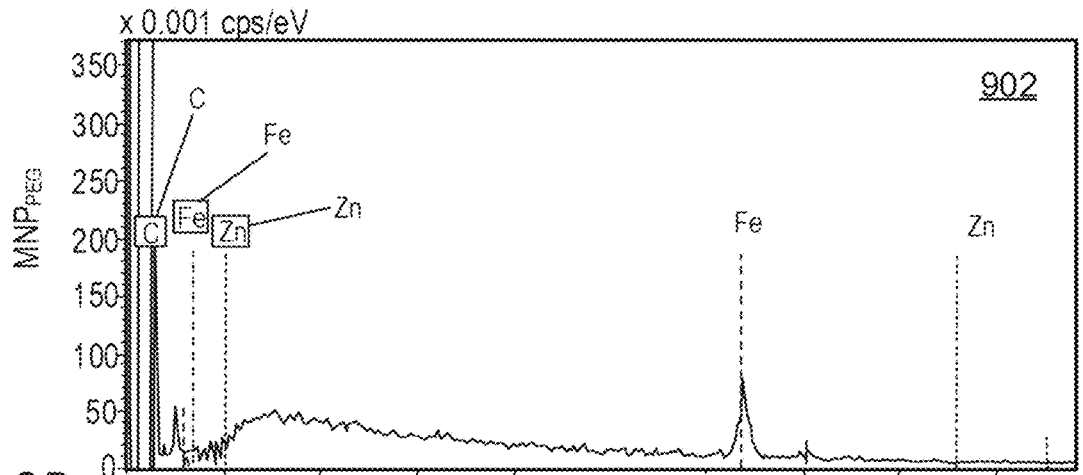
Figure 9C:
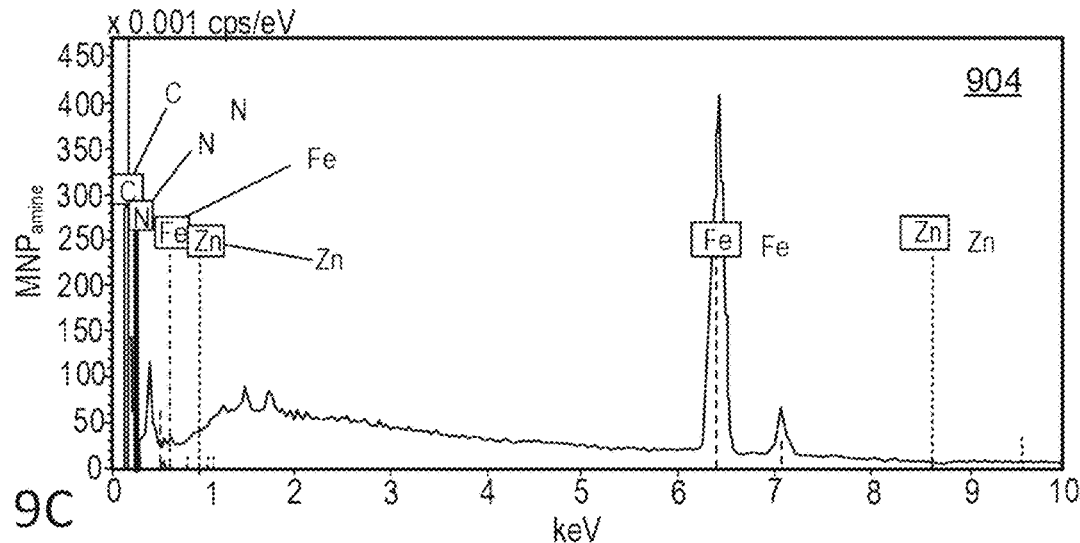

EDS was performed for samples prepared from the following nanoparticle compositions mixed with $Zn(NO_3)_2$: $NP_{PEG-DPA}$, $NP_{PEG}$, and unmodified nanoparticles. FIGS. 9A, 9B, and 9C show EDS spectra 900, 902, 904, respectively, for each of these samples. A significant Zn signal was detected in the spectrum 900 the $NP_{PEG-DPA}$ sample; the $NP_{PEG}$ and unmodified nanoparticle spectra showed only trace amounts of Zn. Secondary electron mode SEM images and EDS images of iron and zinc on these samples show the presence of iron in all three samples but confirm that zinc is present only in the $NP_{PEG-DPA}$ sample. Furthermore, the overlap of the iron and zinc signals in the EDS images for the $NP_{PEG-DPA}$ sample indicate the chelation of $Zn^{2+}$ with bis-DPA in this sample. These results confirmed that both bis-Zn-DPA-PEG and PEG were successfully immobilized on the surface of nanoparticles.

Example 2—Fluorescence Visualization of E. coli Binding to Nanoparticles

Fluorescence-labeled E. coli were used to demonstrate the binding capability of $NP_{PEG-DPA-Zn}$. A bacterial cell culture was prepared by inoculating 25 mL of standard lysogeny broth (LB) with E. coli (E. coli strain Stbl3, Life Technologies, Grand Island, N.Y.) using standard sterile technique. This culture was incubated for 12-18 hours at 37° C. and 5.0% $CO_2$ and agitated at 200 RPM in an orbital shaker incubator overnight. Before using the bacteria for experiments, cells were pelleted by centrifugation at 2,000 g for 5 minutes. The supernatant was discarded and the cell pellet was resuspended in phosphate buffered saline (PBS). The concentration of E. coli was re-adjusted to be $1.0 \times 10^9$ CFU/mL ($OD_{600}$=1.0).

To label the E. coli with the green fluorescent label SYTO 9™ (Life Technologies, Grand Island, N.Y.), which selectively labels live bacteria, the E. coli solution was incubated with 300× diluted SYTO 9 for 30 minutes at room temperature, followed by centrifugation and redispersion in PBS. The labeled E. coli ($1.0 \times 10^7$ CFU/mL) and nanoparticles ($1.0 \times 10^{11}$/mL) were mixed in PBS and incubated for one minute at room temperature. This concentration of bacteria was selected based on the reported peak blood concentration of E. coli after injection of a lethal dose (LD 100) in vivo. 10 μL of this mixture was added to a cell counting chamber for visualization by optical microscopy.

An external permanent magnet was applied to the chamber and dragged across its bottom surface, causing clusters of $NP_{PEG-DPA-Zn}$ co-localized with E. coli to migrate up several centimeters. Phase contrast and green fluorescent images were taken of the chamber using Olympus FSX100 (Olympus, Japan) to check the co-localization of MNPs and E. coli.

Referring to FIGS. 10A-10C, the co-localization of $NP_{PEG-DPA-Zn}$ and E. coli was evidenced by the overlap of a phase contrast image 150 (FIG. 10A) showing $NP_{PEG-DPA-Zn}$ and a green fluorescent image 152 (FIG. 10B) showing E. coli. The co-localization can also be seen clearly in an overlay image 154 (FIG. 10C) including both phase contrast and fluorescent image data. This overlap is indicative of the binding of $NP_{PEG-DPA-Zn}$ to E. coli. The scale bar in all images of FIG. 10 denotes 100 μm.

Referring to FIGS. 10D-10F, a mixture of green fluorescence-labeled E. coli and $NP_{PEG}$ was also prepared and the same magnetic experiment was conducted. No co-localization of E. coli and $NP_{PEG}$ was observed, as can be seen from the lack of overlap between a phase contrast image 156 (FIG. 10D) showing $NP_{PEG}$ and a green fluorescence image 158 (FIG. 10E) showing E. coli. An overlay image 160 (FIG. 10F) also shows that there is no significant overlap between E. coli and $NP_{PEG}$. This lack of overlap indicates that there is no interaction between the PEG chains and the E. coli, and also suggests that complete passivation of the amine groups on the surface of the nanoparticles has occurred.

The specificity of the binding between bis-Zn-DPA and E. coli was further demonstrated by adding fluorescein (FITC)-labeled bis-Zn-DPA-PEG molecules (bis-Zn-DPA-PEG-FITC) to unlabeled E. coli. Fluorescence probes (100 μM), including bis-Zn-DPA-PEG-FITC, FITC-labeled bis-DPA-PEG, FITC-labeled Zn—$NH_2$-PEG, and FITC-labeled $NH_2$-PEG, were each mixed with a sample of unlabeled E. coli ($1.0 \times 10^7$ CFU/mL). After 30 minutes of incubation, each sample was washed twice with PBS and imaged under optical and fluorescence microscopy.

After adding bis-Zn-DPA-PEG-FITC to E. coli, fluorescence microscopy showed that most E. coli were stained with green fluorescence, confirming the binding of bis-DPA-PEG-FITC to E. coli. Minimal fluorescence was detected when FITC-labeled bis-DPA-PEG (without $Zn^{2+}$) was added to E. coli, indicating that Zn participates in the specific binding to E. coli. FITC-labeled PEG and FITC-labeled amine molecules also did not stain E. coli effectively regardless of the addition of Zn, indicating that binding of these molecules to E. coli was minimal.

Example 3—Separation of E. Coli from a Buffer Solution

The efficiency of modified nanoparticles to separate a fixed concentration of E. coli ($1.0 \times 10^7$ CFU/mL) by magnetic separation was measured in phosphate buffered saline (PBS) with varying concentrations of $NP_{PEG-DPA-Zn}$ and $NP_{PEG}$ (from 0 to $1.0 \times 10^1$/mL). Each mixture of E. coli and nanoparticles was incubated in a 1.5 mL test tube for one minute at room temperature and a permanent magnet was placed on the side of the test tube for 2 minutes. 10 µL of the supernatant was collected and added to a cell counting chamber for analysis.

The number of bacteria in a 100× green fluorescence image of the supernatant was counted (using the NIH-provided freeware ImageJ) and converted to E. coli concentration in the solution. For this, a standard curve was generated that correlated the number of E. coli in the 100× green fluorescence image with the E. coli concentration in the solution (see below).

Figure 11:
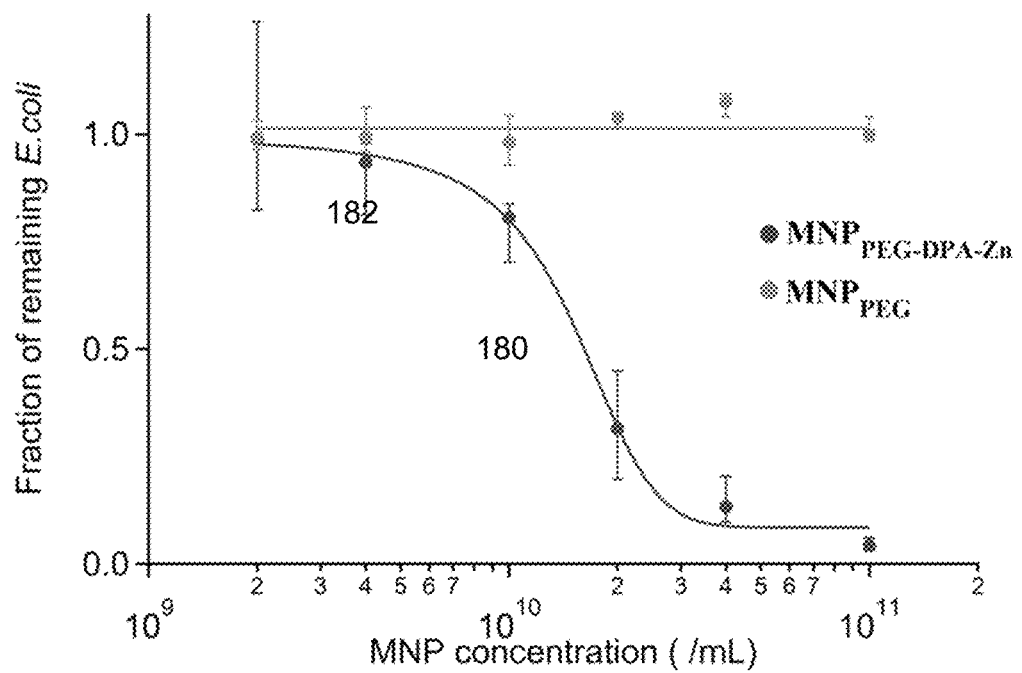
FIG. 11 is a plot of the concentration of *E. coli* after magnetic separation.
Figure 12:
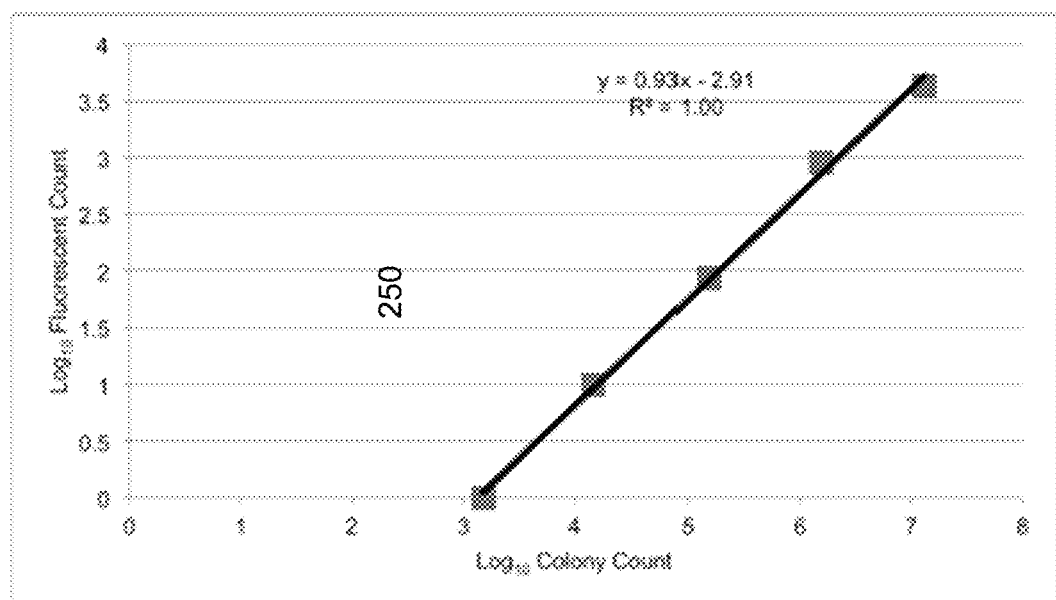
FIG. 12 is a plot showing a correlation between fluorescent labeling analysis and colony counting analysis.

Referring to FIG. 11, a concentration of $1.4 \times 10^{10}$/mL of $NP_{PEG-DPA-Zn}$ removed 50% of E. coli and a concentration of $1.0 \times 10^1$/mL of $NP_{PEG-DPA-Zn}$ completely cleared E. coli from the solution (curve 180). In contrast, $NP_{PEG}$ did not remove E. coli even at the highest MNP concentration (curve 182). In FIG. 12, E. coli concentrations were normalized to the E. coli concentration prior to separation. The data were fitted with a sigmoid curve and a straight line with a zero slope for curves 180 and 182, respectively. Data are medians with $25^{th}$ and $75^{th}$ percentiles (N=4).

The enumeration of bacteria using fluorescent labeling and microscopic analysis is a facile and reliable alternative to colony counting. To identify a correlation between the fluorescent and the colony-counting methods, ten-fold serial dilutions (1:10, 1:100, 1:1,000, 1:10,000, and 1:100,000) of SYTO 9-labeled E. coli in PBS ($OD_{600}$=1.0, $1.0 \times 10^9$ CFU/mL) were used to count the number of bacteria in solution using fluorescent microscopy and bacterial culture on agar plates. For fluorescent counting, 10 µL of each bacterial cell solution was added to a Countess™ cell counting chamber slide (Life Technologies, Grand Island, N.Y.), and the number of bacteria in a 40× green fluorescence image was counted using ImageJ. For bacterial culture and subsequent colony counting, each bacterial solution was further diluted and 200 µL of the diluted bacterial solution was plated onto an LB-agar plate such that 200-300 colony forming units grew per plate. Four plates were created for each serially diluted bacterial cell solution. The two types of bacterial cell count data were plotted against each other on a logarithmic scale to confirm linearity, as shown in a plot 250 of FIG. 12.

In this example and in other examples described herein, a normal distribution of data was not assumed due to the asymmetric distribution of some of the data. Data were analyzed by the non-parametric Mann-Whitney U-test. A p value <0.05 was considered statistically significant unless stated otherwise. For multiple comparisons, Kruskal-Wallis tests were performed followed by Bonferroni corrections.

Example 4—Separation of Endotoxins from a Buffer Solution

To study the ability of $NP_{PEG-DPA-Zn}$ to remove endotoxins, magnetic separation of endotoxins from solution was performed in a test tube with various concentrations of $NP_{PEG-DPA-Zn}$ and $NP_{PEG}$. Nanoparticles (with concentrations ranging from $4.0 \times 10^4$ to $2.0 \times 10^6$/mL) were added to a standard endotoxin solution in PBS of 1.0 EU/mL in 1:1 volume ratio (ToxinSensor™ Chromogenic LAL Endotoxin Assay Kit (Genscript USA Inc., Piscataway, N.J.). After incubation for 1 minutes at room temperature in a test tube, an external magnetic field was applied, separating the nanoparticles from the solution. The remaining solution was collected and endotoxins in the collected solution were measured by using the ToxinSensor™ Chromogenic LAL Endotoxin Assay Kit.

Figure 13:
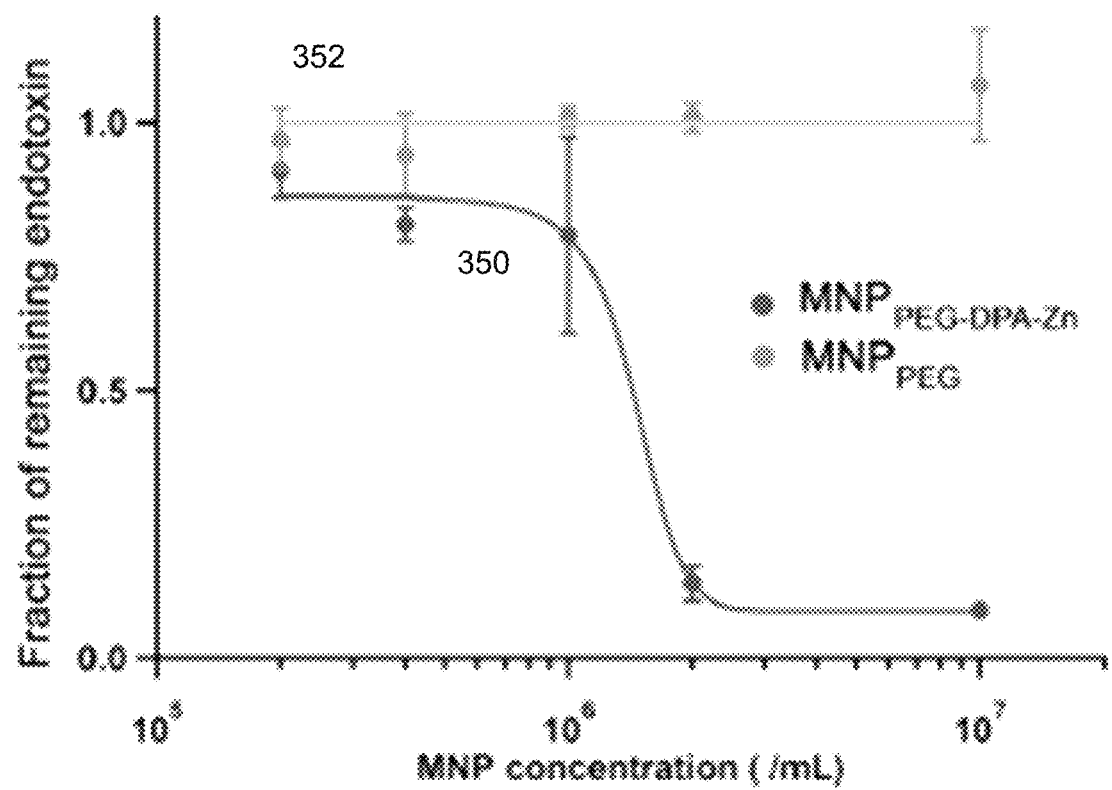
FIG. 13 is a plot of the concentration of endotoxin after magnetic separation.

Referring to FIG. 13, $NP_{PEG-DPA-Zn}$ decreased the concentration of free endotoxin in PBS as the concentration of $NP_{PEG-DPA-Zn}$ increased, to as low as 9.0% of the starting concentration (curve 350). $NP_{PEG}$ did not affect the free endotoxin concentration at any nanoparticle concentration (curve 352). These results demonstrate that $NP_{PEG-DPA-Zn}$ can separate endotoxins from solution through magnetophoresis. In FIG. 14, endotoxin concentrations were normalized to the endotoxin concentration prior to separation. The data were fitted with a sigmoid curve and a straight line with a zero slope for curves 350 and 352, respectively. Data are medians with 25th and 75th percentiles.

Example 5—Separation of E. coli from Blood in a Microfluidic System

The feasibility of using $NP_{PEG-DPA-Zn}$ to remove bacteria from blood was tested for bovine blood (Bovine whole blood with heparin (0.5 U/mL), Sierra for Medical Science, Whittier, Calif.) diluted to a red blood cell (RBC) concentration of $1.0 \times 10^8$/mL. This concentration, approximately 50 times lower than that of adult human blood (~$5.0 \times 10^9$/mL), was used because higher RBC concentrations obstructed microscopic imaging after magnetic separation. Any changes in the RBC concentration after magnetic separation indicate the degree of non-specific binding between nanoparticles and RBCs.

Nanoparticles ($1.0 \times 10^{11}$/mL) and E. coli ($1.0 \times 10^7$ CFU/mL) were mixed with bovine RBC solution ($1.0 \times 10^8$/mL) and incubated for one minute at room temperature. After magnetic separation in a test tube as described above, green fluorescence and phase contrast images were used to count the number of E. coli and RBCs, respectively. After the first round of separation was performed, fresh nanoparticles were added to the solution, and another round of magnetic separation was performed. This process was repeated until no E. coli were found in the solution.

Figures 14A, 14B:
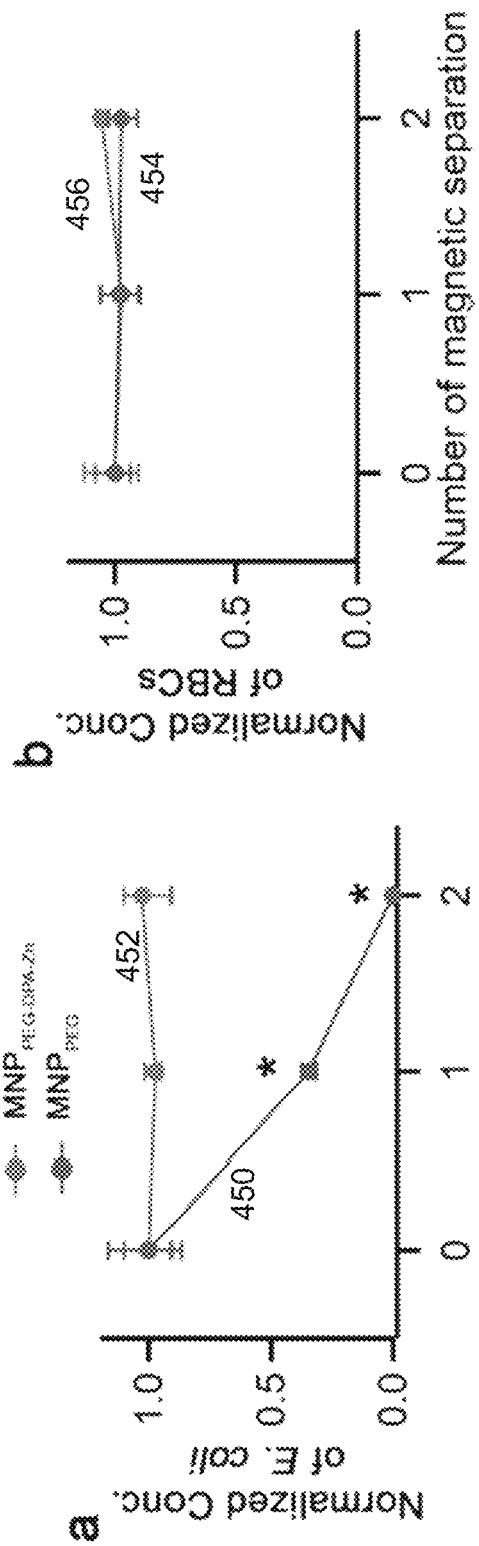
FIGS. 14A and 14B are plots of the concentration of *E. coli* and red blood cells in whole blood after magnetic separation.

Referring to FIG. 14A, $NP_{PEG-DPA-Zn}$ (curve 450) removed about 70% of E. coli from the blood sample during a first cycle, a 30% decrease in the amount of removed E. coli compared to the same separation process conducted in PBS (FIG. 11). A second round of magnetic separation on the same blood sample with fresh $NP_{PEG-DPA-Zn}$ resulted in complete removal of E. coli from the blood sample. Referring to FIG. 14B, the number of RBCs did not change during these separations (curve 454), indicating negligible nonspecific interactions between $NP_{PEG-DPA-Zn}$ and RBCs. Similar experiments with $NP_{PEG}$ did not alter the numbers of E. coli (curve 452) or RBCs (curve 456) after either the first or the second separation, indicating that $NP_{PEG}$ are incapable of selectively separating E. coli and that $NP_{PEG}$ do not bind non-specifically to RBCs. In FIGS. 14A and 14B, RBC concentrations were normalized to their concentrations prior to separation. Data are medians with 25th and 75th percentiles. * indicates p<0.05 compared to the initial concentrations.

A hemolysis assay confirmed that minimal damage was done to RBCs by $NP_{PEG-DPA-Zn}$ or $NP_{PEG}$. To evaluate the degree hemolysis induced by the presence nanoparticles, RBCs were collected from bovine whole blood by centrifugation at 2,000 g for 15 minutes. Saline was added to the concentrated RBC solution to recover the original RBC concentration. Nanoparticles ($1.0 \times 10^{11}$/mL of $NP_{PEG-DPA-Zn}$ and $NP_{PEG}$) were added to the RBC solution. As a negative control, in which RBCs were known not be harmed, saline was added to the RBC solution instead of nanoparticles. As a positive control, in which all RBCs are lysed, Triton X-100 (1.0% v/v) was added to the RBC solution. After incubation at 4° C. for 30 minutes, the RBC mixtures were centrifuged at 15,000 g for 5 minutes and the absorbance (Abs) of the supernatant at 541 nm (an absorbance peak of hemoglobin) was measured.

The percentage of hemolysis was calculated by the following equation:

$$\% \text{ hemolysis} = \frac{Abs \text{ of sample} - Abs \text{ of negative control}}{Abs \text{ of positive control} - Abs \text{ of negative control}} \times 100$$

Referring to Tables 2 and 3, neither $NP_{PEG}$ nor $NP_{PEG-DPA-Zn}$ caused any significant hemolysis. Data in Table 2 are the mean absorbance at 541 nm with standard deviations of the supernatants from the hemolysis assay described above. Data in Table 3 are means with standard deviations. All samples were diluted ten times before measurement (N=4).

TABLE 2

Absorbance at 541 nm from exposure to nanoparticles, with controls

| Agent | Triton X-100 | Saline | NPPEG | $NP_{PEG-DPA-Zn}$ |
|---|---|---|---|---|
| Abs at 541 nm | 0.837 ± 0.052 | 0.093 ± 0.003 | 0.915 ± 0.002 | 0.09475 ± 0.002 |

TABLE 3

Percentage of hemolysis from exposure to nanoparticles calculated using the equation above

| Agent | $NP_{PEG}$ | $NP_{PEG-DPA-Zn}$ |
|---|---|---|
| % Hemolysis | −0.23 ±0.35 | 0.20 ± .022 |

Example 6—Separation of E. coli in a Network of Microfluidic Systems

A microfluidic system (1,000 μm width×200 μm height) was fabricated by casting poly(dimethylsiloxane) (PDMS, Dow Corning, Midland, Mich.) onto a silicon substrate with channels patterned with SU-8 (Microchem, Newton, Mass.). After curing the PDMS at 65° C. for 2 hours, inlets and outlets for fluids were created using a 1.0 mm biopsy punch. To hold the disk magnets (12.5 mm diameter×5.0 mm height, NdFeB, 3.4×10-3 G (gauss) in 1.0 mm, Indigo Instruments, Canada) in position, three 12-mm holes were created 2.5 mm from the channel, in series along the direction of flow in the microchannel. The PDMS slab with the pattern of microchannels was subsequently sealed onto glass (Dow Corning).

Referring again to FIG. 5, in the dual inlet microfluidic system 600, saline (9.0% NaCl, w/v) was injected into inlet A. A mixture of RBCs ($1.0 \times 10^8$ RBC/mL), fluorescence-labeled E. coli ($1.0 \times 10^7$ CFU/mL), and $NP_{PEG-DPA-Zn}$ or $NP_{PEG}$ nanoparticles ($1.0 \times 10^{11}$ particles/mL) was injected into inlet B. Three permanent magnets 610 were placed along the main channel to effect magnetophoric separation of E. coli from the saline. Liquid exited the system through outlets C and D. A flow rate of 9.0 mL/hour was used.

Referring to FIGS. 15A-15E, the migration of RBCs and labeled E. coli was visualized by phase contrast and fluorescence microscopy for a variety of flow conditions. In these images, the clear layer of flow was saline and the turbid layer contained nanoparticles, RBCs, and E. coli. Nanoparticles appear dark in phase contrast images; E. coli appear bright in fluorescence images. The top and bottom flow channel branches at the right of each image point to outlets C and D, respectively, of the microfluidic system.

Images 550a and 550b (FIG. 15A) correspond to the flow of a solution including $NP_{PEG-DPA-Zn}$ with no magnet present along the channel. Without a magnetic field, nanoparticles, RBCs, and E. coli exited the channel through outlet D.

Images 552a and 552b (FIG. 15B) and images 554a and 554b (FIG. 15C) correspond to the flow of a solution including with the magnet present along the channel. With a magnetic field, E. coli that had bound to $NP_{PEG-DPA-Zn}$ were pulled toward the magnet and exited through outlet C. A significant portion of the E. coli and nanoparticles also clustered around the magnet (FIG. 15C) rather than exiting through outlet C.

Images 556a and 556b (FIG. 15D) correspond to the flow of a solution including $NP_{PEG}$ for the control situation in which no magnet was present along the channel. Images 558a and 558b (FIG. 15E) correspond to the flow of a solution including $NP_{PEG}$ with the magnet present along the channel. The bulk of the turbid layer of flow was unaffected by the magnetic field and exited through outlet D. E. coli did not migrate toward outlet C nor did E. coli cluster around the magnet.

Figure 16:
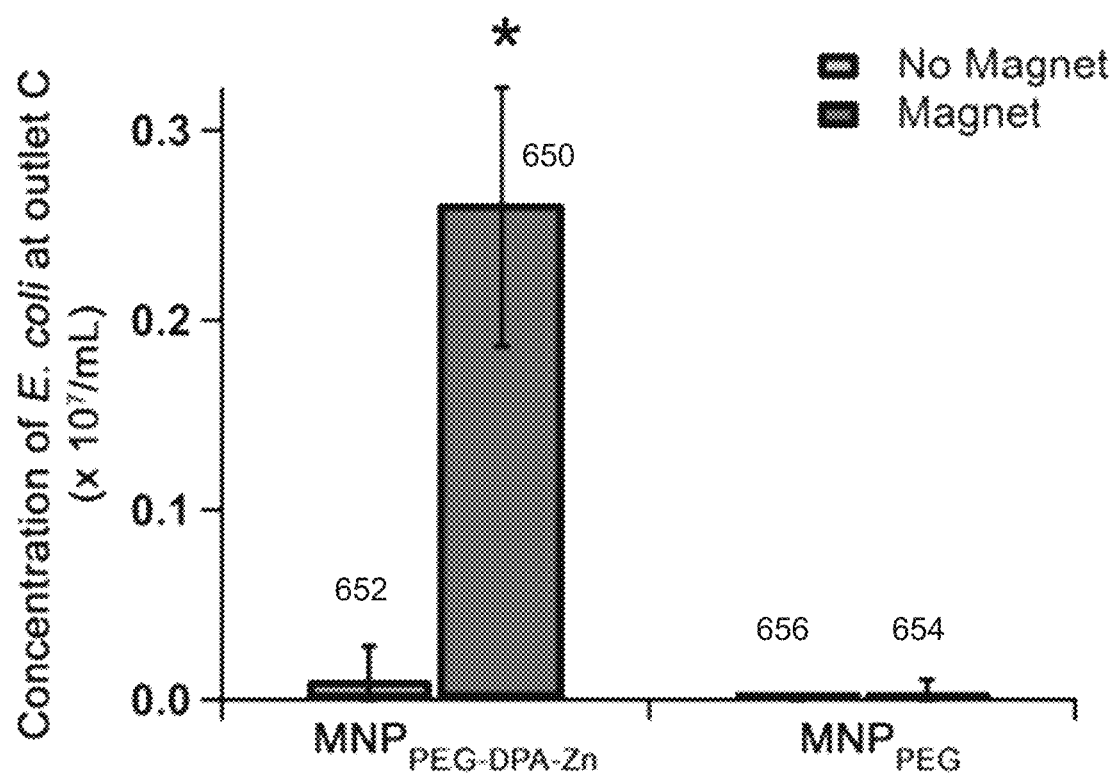
FIG. 16 is a plot of the concentration of *E. coli* after passing through a dual inlet microfluidic system.

Referring to FIG. 16, the E. coli concentration was measured at outlet C for flows including $NP_{PEG-DPA-Zn}$ and $NP_{PEG}$. About 25% of the original concentration of E. coli was measured at outlet C after a single pass of the mixture through the dual inlet system in the presence of the magnet (bar 650); no E. coli were observed with no magnet (bar 652). No E. coli were observed with (bar 654) or without (Bar 656) the magnet for mixtures containing $NP_{PEG}$. Data are medians with 25th and 75th percentiles. * indicates p<0.05 compared to $NP_{PEG}$ with no magnet.

The dual inlet system was also used for separation of E. coli from whole blood. Although more E. coli were found to be associated with $NP_{PEG-DPA-Zn}$ than with $NP_{PEG}$ at outlet C when using whole blood, many RBCs, E. coli, and nanoparticles also exited through outlet C even in the absence of a magnetic field. This result may be due to the difficulties in maintaining two symmetric laminar flows when using whole blood, which has a larger viscosity than saline (viscosity=1 cP for saline, 10 cP for blood).

Referring again to FIG. 6, a single inlet, dual outlet microfluidic system 600 was prepared by closing the inlet A. Nanoparticles ($1.0 \times 10^{11}$/mL) and fluorescence-labeled E. coli ($5.0 \times 10^6$ CFU/mL) were mixed with whole blood and injected into inlet B at 9.0 mL/hour. Three permanent magnets were placed along the main channel to effect magnetophoric separation of E. coli from whole blood. Liquid exited the system through outlets C and D and the liquid exiting through outlet D was collected and analyzed with fluorescent microscopy. All experiments were performed at 4° C. to prevent blood coagulation.

Figures 17A, 17B, 17C:
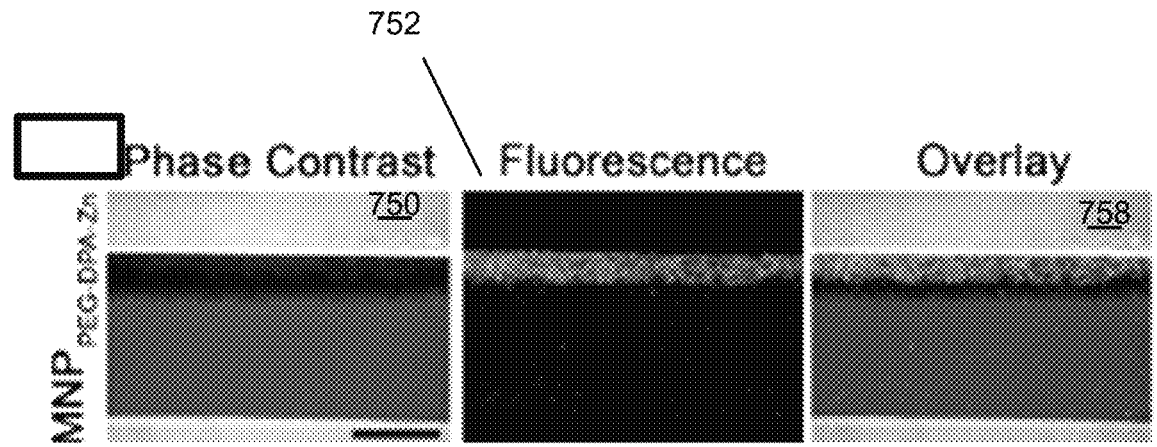
FIGS. 17A-17F are phase contrast, green fluorescent, and overlay images of nanoparticles and *E. coli* in a single inlet microfluidic system.
Figures 17D, 17E, 17F:
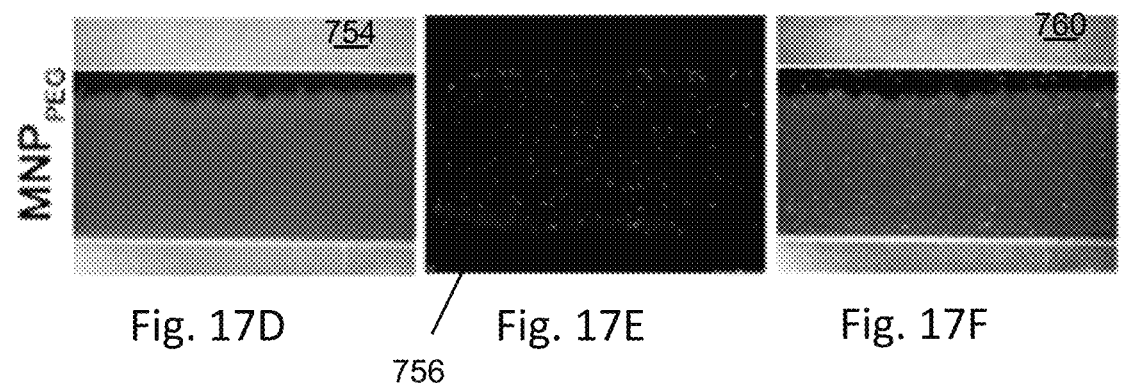

Referring to FIG. 17A-17F, the colocalization of $NP_{PEG\text{-}DPA\text{-}Zn}$ (FIGS. 17A and 17B) or $NP_{PEG}$ (FIGS. 17D and 17E) with fluorescence-labeled E. coli within the main channel of the microfluidic system was visualized by phase contrast and fluorescence microscopy, respectively. Overlay images show the overlap between the corresponding phase contrast and fluorescence images for $NP_{PEG\text{-}DPA\text{-}Zn}$ (FIG. 17C) and $NP_{PEG}$ (FIG. 17F). These images demonstrate that $NP_{PEG\text{-}DPA\text{-}Zn}$ are co-located with E. coli near the magnets, while $NP_{PEG}$ accumulated near the magnets without E. coli.

Figure 18:
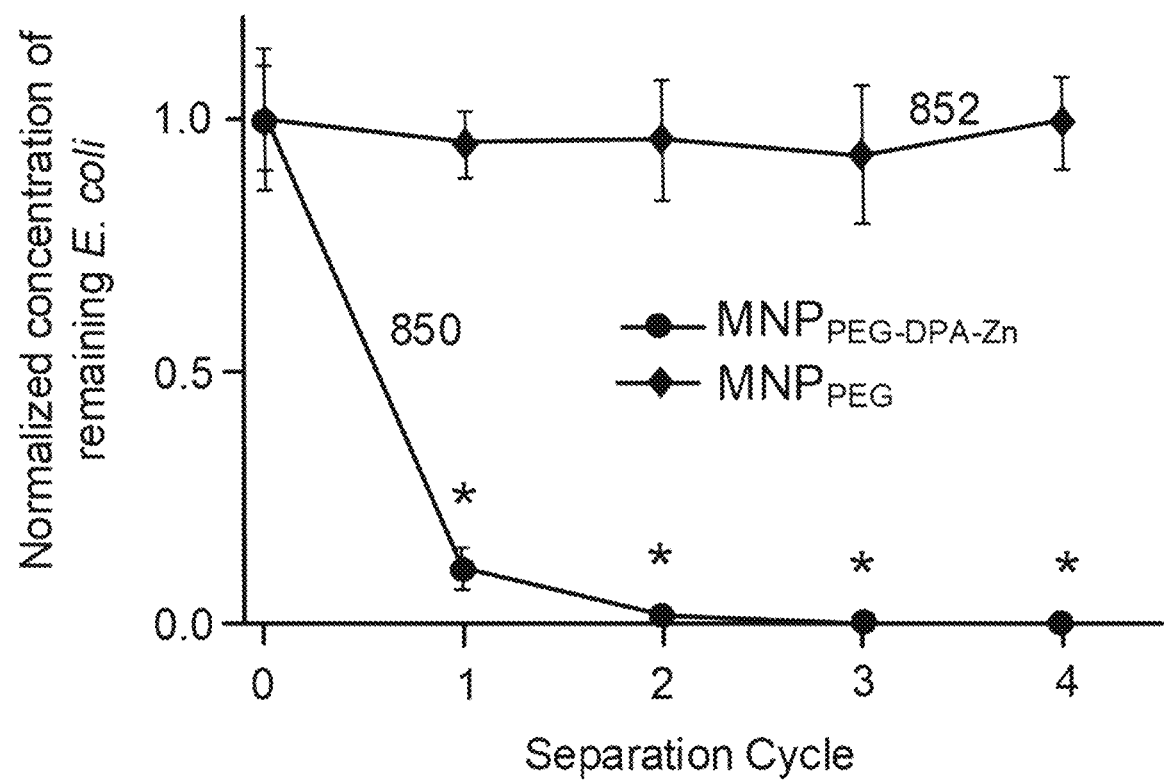
FIG. 18 is a plot of the concentration of *E. coli* after passing through a single inlet microfluidic system.
Figure 19A:
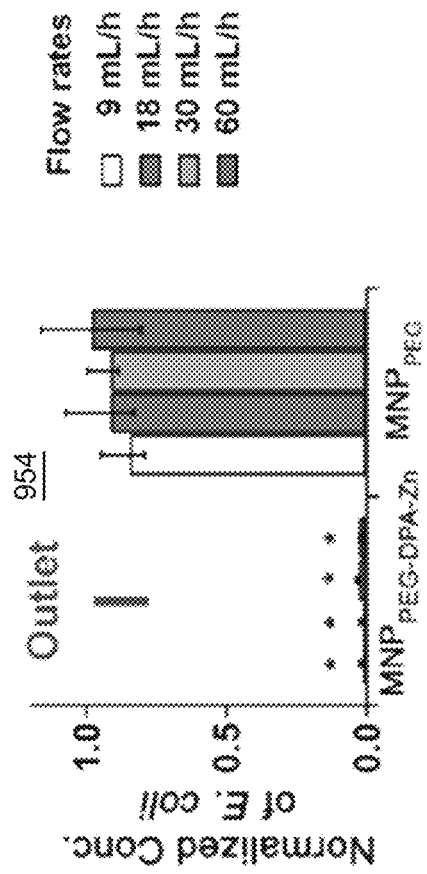
FIG. 19A-19D are a series of plots of the concentration of *E. coli* after passing through a network of microfluidic systems at various flow rates.
Figure 19C:
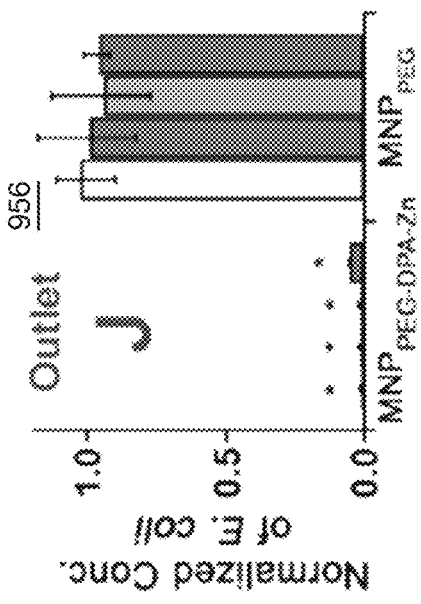
Figure 19B:
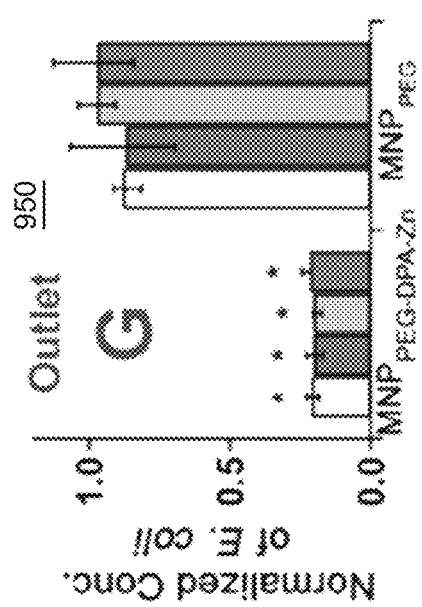
Figure 19D:
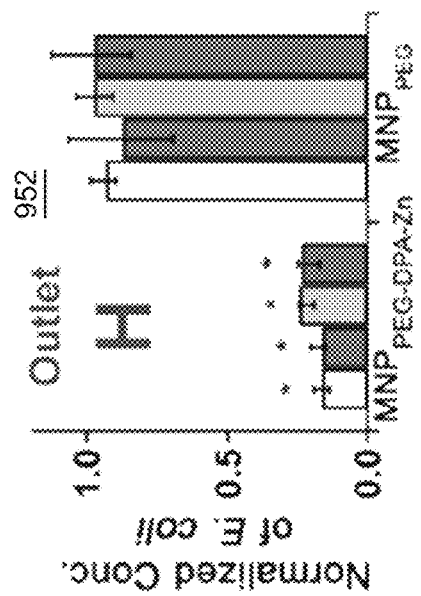

Referring to FIG. 18, after each pass through the single inlet microfluidic system, the solution was collected at outlet D and re-infused at inlet B with a fresh infusion of nanoparticles. This process was repeated four times. For solutions containing $NP_{PEG\text{-}DPA\text{-}Zn}$, all E. coli had been separated from whole blood within two cycles of separation through the microfluidic system (curve 850). For solutions containing $NP_{PEG}$, no change in the E. coli population was observed (curve 852). In FIG. 18, the concentration of E. coli in whole blood at outlet C was normalized to the initial E. coli concentration. Data are medians with 25th and 75th percentiles (N=4). * indicates $p<0.01$ compared to the initial concentration.

The effectiveness of microfluidic separation was enhanced by flowing blood through a nested microfluidic system formed by connecting multiple individual microfluidic systems in series and in parallel. In the nested microfluidic system, multiple magnetic separations could be completed in a single pass. Referring again to FIG. 7, the nested system 700 had a single inlet B, through which a mixture of E. coli ($5.0 \times 106$ CFU/mL), nanoparticles ($1.0 \times 1011$/mL), and whole blood was injected. Blood exiting the system 700 at various outlets was collected and the concentration of E. coli in each sample was determined. Blood exiting through outlets G and G had passed through two magnetic separation sites; blood exiting through outlets I and J had passed through three magnetic separation sites. Various flow rates (9, 18, 30, and 60 mL/hour) of blood through the system were tested.

Referring to FIGS. 19A-19D, the concentration of E. coli at sites G, H, I, and J was determined for each flow rate and is shown in graphs 950, 952, 954, 956, respectively. For solutions containing $NP_{PEG\text{-}DPA\text{-}Zn}$, the concentration of E. coli in blood exiting through outlets G and H was about 20% of the starting concentration for all flow rates. Much lower concentrations (<5%) were found in blood exiting through outlets I and J. These significant reductions in bacterial concentration were reproduced for flow rates as high as 60 mL/hour. There was no statistically significant difference between concentrations at G and H or between concentrations at I and J. There was also no statistically significant difference in concentrations for the four flow rates.

For solutions containing $NP_{PEG}$, E. coli concentrations remained substantially the same as the initial E. coli concentration regardless of the position of the outlet or the flow rate. In FIGS. 19A-19D, the concentration of E. coli in whole blood at each outlet was normalized to the initial E. coli concentration. Data are medians with 25th and 75th percentiles (N>5). * indicates $p<0.05$ compared to the initial concentration.

Example 7—Protocol for In Vivo Separation

To demonstrate that bacterial separation can work for in vivo systems, an animal model protocol was developed. PDMS "chips" including multiple parallel microfluidic channels were prepared. The microfluidic channel design emulated capillary microcirculation, which maintains the viability of fragile circulating red and white blood cells as well as preventing thrombosis (clot). The channel diameter was determined based on a balance between having sufficiently large channel diameters to minimize shear stress and flow irregularities and the loss of functional surface area that results from increasing diameter.

To demonstrate that bacterial separation/filtration system and extracorporeal circuitry works in vivo, an established rat model of septic rats placed onto cardiopulmonary bypass circuits can be used. Adult male Sprague-Dawley rats can be rendered septic by cecal ligation and puncture (i.e. their bowel will be punctured to induce septic shock), mechanically ventilated, and then cannulated at the femoral vein (to drain blood) and jugular vein (to return blood). By this paradigm, blood is removed from the body, pumped through bacteria separation system, and returned to the body. Bacterial cells can be quantified before and after treatment by counting the number of colonies forming on bacterial plate cultures. Further, concentration of endotoxin in the blood can be determined using commercially available assays.

Example 8—Ligand Synthesis

Figure 20:
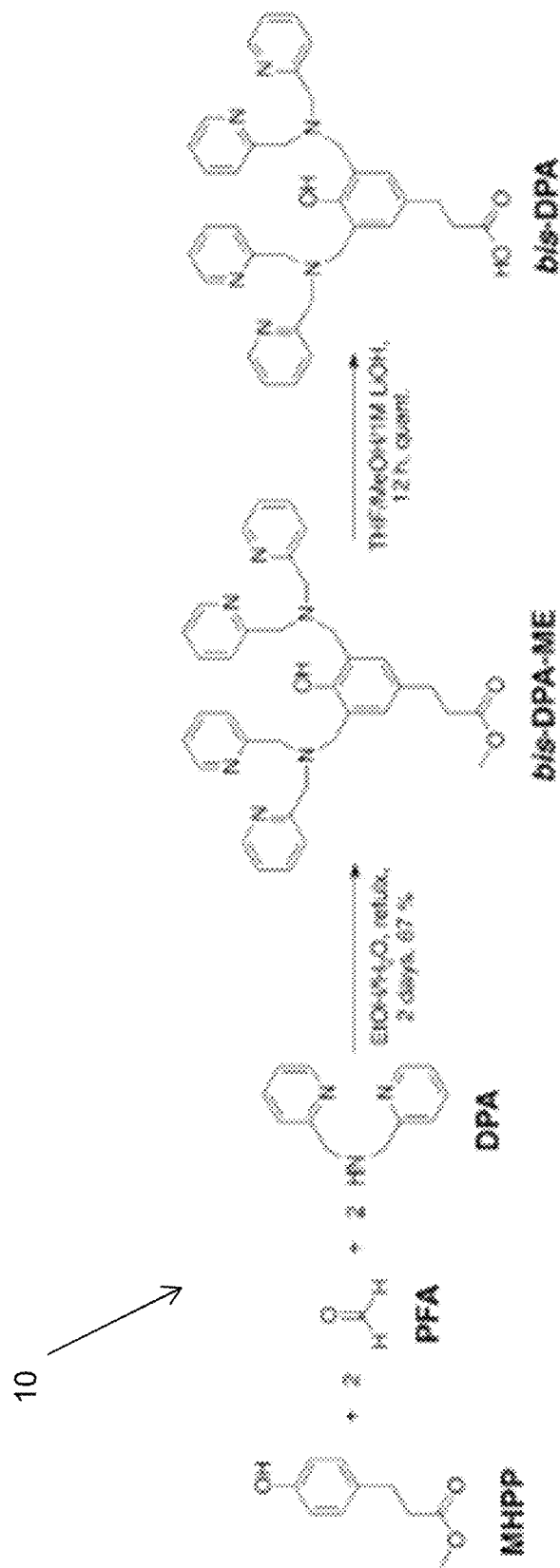
FIG. 20 is a scheme for the synthesis of bis-DPA.

FIG. 20 shows a scheme 10 for the synthesis of 3-(3,5-bis((bis(pyridin-2-ylmethyl)amino)methyl)-4-hydroxyphenyl) propanoic acid (bis-DPA). Paraformaldehyde (PFA, 0.55 g, 18 mmol) and di(2-picolyl)amine (DPA, 2.8 g, 14 mmol) were placed in a 250 mL round bottom flask and suspended in a mixture of ethanol (15 mL) and water (45 mL). Commercially available methyl 3-(4-hydroxyphenyl) propanoate (MHPP, 1.0 g, 5.6 mmol) and hydrochloric acid (HCl, 1.0 M, 1.4 mL) were added to the mixture and refluxed for 2 days. After the reaction mixture was cooled to room temperature, it was neutralized with saturated $Na_2CO_3$ and the aqueous solution was extracted with excess chloroform. An organic phase was dried over $Na_2SO_4$ and chloroform was evaporated under reduced pressure. The crude product was purified by column chromatography on silica gel (MeOH:$CHCl_3$ 5:95) to obtain methyl 3-(3,5-bis((bis(pyridin-2-ylmethyl)amino)methyl)-4-hydroxyphenyl)propanoate, bis-DPA-methyl ester (bis-DPA-ME) as a pale yellow oil (2.4 g, 4.0 mmol, 71%).

A solution of bis-DPA-ME (2.4 g, 4.0 mmol) in tetrahydrofuran (THF, 330 mL) and methanol (210 mL) was added to a LiOH solution (aq., 2.0 M, 200 mL). The mixture was stirred for 12 hours at room temperature and then poured into chloroform (300 mL). After acidification with HCl (1.0 M), the aqueous layer was extracted with excess chloroform and the organic phase was dried over $Na_2SO_4$. Bis-DPA was obtained without further purification after complete evaporation of chloroform.

The synthesis of bis-DPA was confirmed by $^1H$ nuclear magnetic resonance (NMR) spectroscopy in DMSO-$d_6$ (400

MHz, Varian), as shown in the NMR spectrum S200 of FIG. S2. The peaks were identified as follows: δ 10.89 (bs, 1H), 8.48 (d, 4H), 7.68 (t, 4H), 7.46 (t, 4H), 7.21 (d, 4H), 7.04 (s, 2H), 3.70 (s, 8H), 3.57 (s, 4H), 2.62 (t, 2H), 2.46 (t, 2H).

Figure 21:
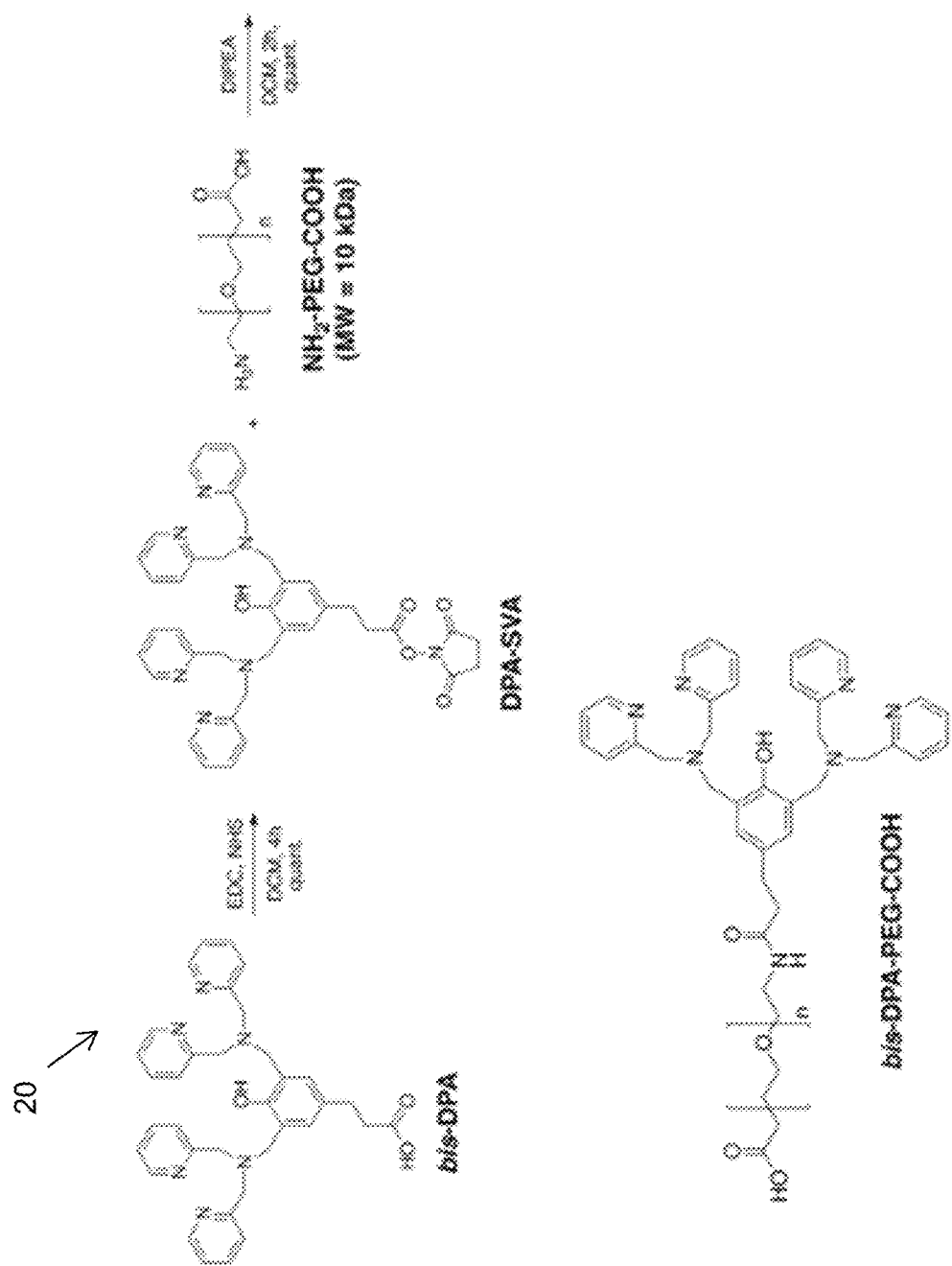
FIG. 21 is a scheme for the synthesis of bis-DPA-PEG-COOH.

FIG. 21 shows a scheme 20 for the synthesis of bis-DPA-PEG-COOH (10 kDa). Bis-DPA (0.1 g, 0.17 mmol), 1-ethyl-3-(3-dimethylaminopropyl)-carbodiimide hydrochloride (EDC, 65 mg, 0.34 mmol) and N-hydroxysuccinimide (NHS, 23 mg, 0.2 mmol) were added to and stirred in dry dichloromethane (10 mL) for 4 hours at room temperature. The solvent was removed under reduced pressure and the crude product was purified by flash chromatography (MeOH:CHCl$_3$ 5:95) to obtain DPA-succinimidyl valerate (DPA-SVA, 76 mg, 0.11 mmol, 65%) as a pale yellow solid. A mixture of NH$_2$-PEG-COOH (10 kDa, 0.92 g, 0.092 mmol, JenKem Technology USA, Allen, Tex.) and DPA-SVA (76 mg, 0.11 mmol) was stirred for 2 hours in dry dichloromethane with N,N-diisopropylethylamine (DIPEA, 32 μL). bis-DPA-PEG-COOH was quantitatively obtained after size exclusion chromatography in chloroform.

The synthesis of bis-DPA-PEG-COOH was confirmed by $^1$H NMR spectroscopy in DMSO-d$_6$ (400 MHz, Varian), as shown in the NMR spectrum S400 of FIG. S4. The peaks were identified as follows: δ 8.43 (d, 4H), 7.93 (bs, 1H), 7.68-7.64 (m, 4H), 7.41 (d, 4H), 7.19-7.16 (m, 4H), 6.96 (s, 2H), 3.94 (s, 8H), 3.63 (m, 8H), 3.44 (s, 960), 3.27 (m, 2H), 2.91 (t, 2H), 2.45 (m, 4H).

Figure 22:
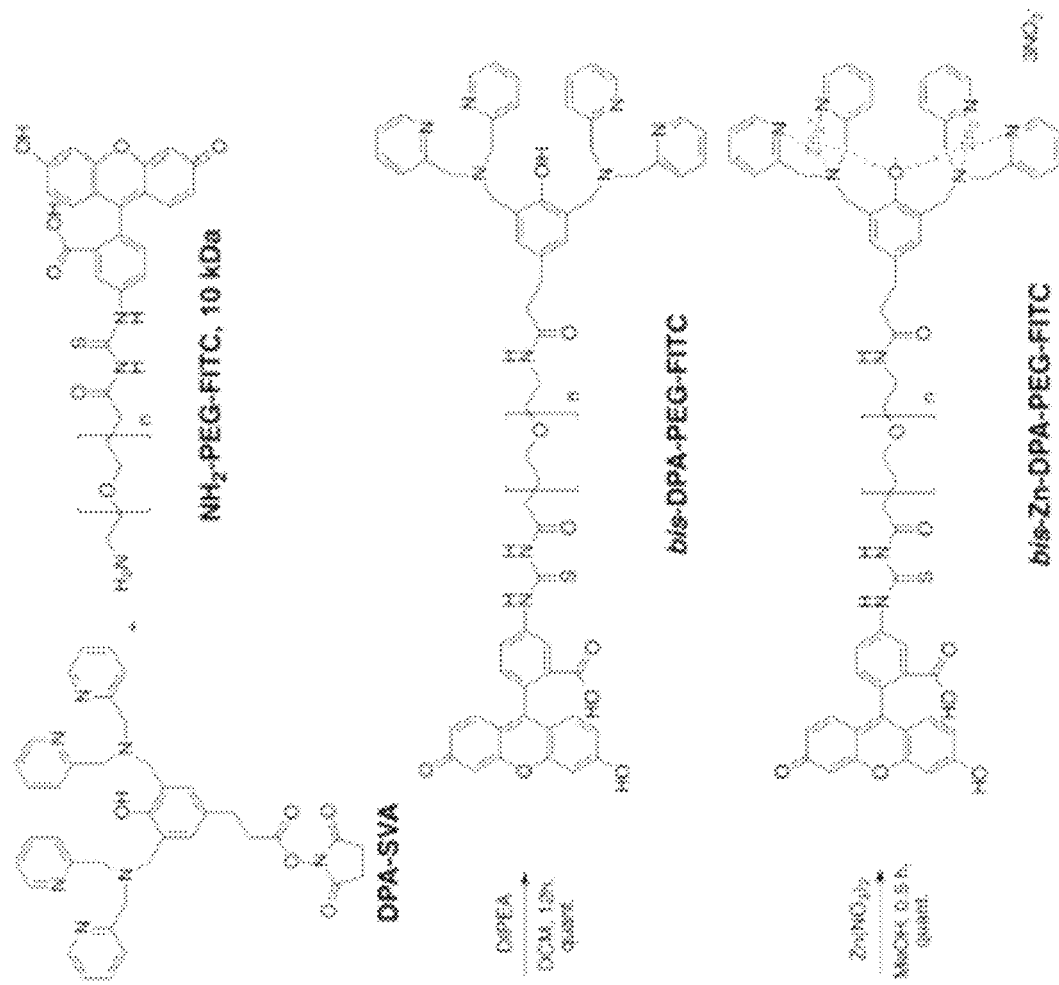
FIG. 22 is a scheme for the synthesis of bis-Zn-DPA-PEG-FITC.

FIG. 22 shows a scheme 30 for the synthesis of bis-Zn-DPA-PEG-FITC (10 kDa). A mixture of NH$_2$-PEGFluorescein isothiocyanate (FITC, 10 kDa, 20 mg, 2.0 μmol) and DPA-SVA (1.6 mg, 2.4 μmol) was stirred for 2 hours in dry dichloromethane with N,N-Diisopropylethylamine (DIPEA, 1.0 μL). bis-DPA-PEG-FITC was quantitatively obtained after size exclusion chromatography in chloroform. bis-DPA-PEG-FITC (20 mg, 2.0 μmol) and zinc nitrate hexahydrate (0.76 mg, 4.0 μmol) were dissolved in methanol (2.0 mL). The mixture was stirred for 1 h at room temperature and the solvent was evaporated under reduced pressure to obtain bis-Zn-DPA-PEG-FITC.

Cu-DPA-Cl$_2$ was synthesized by adding DPA (104 mg, 0.5 mmol) to a solution of CuCl$_2$-2H$_2$O (82 mg, 0.5 mmol) in methanol (20 mL). The mixture was refluxed for one hour, allowed to cool to room temperature, and filtered. The filtration product was allowed to crystallize at room temperature and then filtered and recrystallized from a hot water/acetonitrile (1:1, 10 mL) mixture. From the Cu-DPA-Cl$_2$ product, Cu-DPA-PEG-COOH or Cu-DPA-PEG-FITC can be obtained using standard chemical reactions. Further details about the synthesis and characterization of Cu-DPA-Cl$_2$ can be found in Choi et al., "Synthesis, properties, and X-ray structure of [Cu(dpa)Cl$_2$] (dpa=di-(2-picolyl)amine)," *Journal of Chemical Crystallography*, December 2003, 33:12, pp 947-950, the contents of which are incorporated herein by reference in their entirety.

Unless otherwise specified, chemicals were purchased from Sigma-Aldrich (St. Louis, Mo.) and used without further purification.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nanoparticle configured to bind to a bacterial contaminant, the nanoparticle comprising:
    a core comprising a magnetic material; and
    a plurality of ligands attached to the nanoparticle, wherein the ligands comprise bis(dipicolylamine) coordinated with a zinc ion (bis-Zn-DPA) and wherein the bis-Zn-DPA comprises a hydroxyphenyl, wherein the bis-Zn-DPA can bind to the bacterial contaminant.

2. The nanoparticle of claim 1, wherein the bis-Zn-DPA is attached to the core of the nanoparticle via a spacer having a molecular weight of 10 kDa to 50 kDa.

3. The nanoparticle of claim 2, wherein the spacer comprises a polymer.

4. The nanoparticle of claim 1, wherein the ligands comprise a filler molecule.

5. The nanoparticle of claim 1, wherein the core comprises one or more of a ferrimagnetic material, a ferromagnetic material, an antiferromagnetic material, a paramagnetic material, and a superparamagnetic material.

6. The nanoparticle of claim 1, wherein the core comprises iron oxide.

7. The nanoparticle of claim 1, wherein an external surface of the core comprises a chemical group that can bind to the ligands.

8. The nanoparticle of claim 1, wherein the bis-Zn-DPA can bind to at least one of Gram positive bacteria, Gram negative bacteria, and an endotoxin.

9. A method of separating a bacterial contaminant from a liquid, the method comprising:
    combining the liquid with a plurality of nanoparticles that can bind to the bacterial contaminant, each nanoparticle comprising:
        a core comprising a magnetic material, and
        a plurality of ligands attached to the nanoparticle, the ligands comprising bis(dipicolylamine) coordinated with a zinc ion (bis-Zn-DPA), the bis-Zn-DPA comprising a hydroxyphenyl;
    applying a magnetic field to the liquid including the nanoparticles, including attracting at least some of the nanoparticles by the magnetic field; and
    separating the liquid from the attracted nanoparticles, wherein the bacterial contaminant is bound to at least some of the attracted nanoparticles.

10. The method of claim 9, wherein the liquid includes blood.

11. The method of claim 9, comprising directing the liquid including the nanoparticles through a flow channel.

12. The method of claim 11, wherein directing the liquid through the flow channel includes flowing the liquid through the flow channel with a flow rate up to 70 mL/hour.

13. The method of claim 12, wherein directing the liquid through the flow channel includes flowing the liquid through the flow channel with a flow rate of between 5 mL/hour and 70 mL/hour.

14. The method of claim 9, comprising incubating the liquid including the nanoparticles prior to applying the magnetic field for about five minutes or less.

* * * * *